(12) United States Patent
Haarmann-Thiemann

(10) Patent No.: US 10,531,971 B2
(45) Date of Patent: Jan. 14, 2020

(54) BALLOON CATHETER HAVING HYDRAULIC ACTUATOR

(71) Applicant: ABBOTT CARDIOVASCULAR SYSTEMS INC., Santa Clara, CA (US)

(72) Inventor: Anna Marie Haarmann-Thiemann, Busingen (DE)

(73) Assignee: Abbott Cardiovascular System Inc., Santa Clara, CA (US)

( * ) Notice: Subject to any disclaimer, the term of this patent is extended or adjusted under 35 U.S.C. 154(b) by 508 days.

(21) Appl. No.: 14/767,968

(22) PCT Filed: Nov. 11, 2013

(86) PCT No.: PCT/US2013/069477
§ 371 (c)(1),
(2) Date: Aug. 14, 2015

(87) PCT Pub. No.: WO2014/143203
PCT Pub. Date: Sep. 18, 2014

(65) Prior Publication Data
US 2016/0051386 A1    Feb. 25, 2016

Related U.S. Application Data

(63) Continuation-in-part of application No. 13/797,636, filed on Mar. 12, 2013, now Pat. No. 9,283,101, and
(Continued)

(51) Int. Cl.
*A61F 2/958*    (2013.01)
*A61F 2/966*    (2013.01)
(Continued)

(52) U.S. Cl.
CPC ............. *A61F 2/958* (2013.01); *A61M 25/10* (2013.01); *A61F 2/966* (2013.01);
(Continued)

(58) Field of Classification Search
CPC .... A61F 2/958; A61F 2/966; A61F 2002/011; A61M 25/10; A61M 2025/1081; A61M 2025/105
See application file for complete search history.

(56) References Cited

U.S. PATENT DOCUMENTS 5,534,007 A    7/1996 St. Germain et al.
5,676,654 A    10/1997 Ellis et al.
(Continued)

FOREIGN PATENT DOCUMENTS

EP    1208816 A2    5/2002
JP    11-505162    5/1999

OTHER PUBLICATIONS

U.S. Appl. No. 15/180,655, filed Jun. 13, 2016.
(Continued)

*Primary Examiner* — Anh T Dang
(74) *Attorney, Agent, or Firm* — Baker Botts L.L.P.

(57) ABSTRACT

Catheter including an inner tubular member, an outer tubular member movable relative to the inner tubular member, and an expandable member coupled to the distal end portion of the inner tubular member. The expandable member having an inner chamber and transitionable between a deflated configuration and an inflated configuration. A pressure chamber is defined by the proximal seal, the distal seal, the exterior surface of the inner tubular member and interior surface of the outer tubular member, with the pressure chamber in fluid communication with a fluid flow port, wherein fluid introduced through the fluid flow port and into the pressure chamber applies a force on the proximal seal to urge the outer tubular member in a proximal direction.

22 Claims, 16 Drawing Sheets

Related U.S. Application Data a continuation-in-part of application No. 13/801,588, filed on Mar. 13, 2013, now Pat. No. 9,326,875.

(51) Int. Cl.
*A61M 25/10* (2013.01)
*A61F 2/95* (2013.01)
*A61F 2/01* (2006.01)

(52) U.S. Cl.
CPC . *A61F 2002/011* (2013.01); *A61F 2002/9517* (2013.01); *A61F 2250/0019* (2013.01); *A61F 2250/0021* (2013.01); *A61M 2025/105* (2013.01); *A61M 2025/1081* (2013.01)

(56) References Cited

U.S. PATENT DOCUMENTS

| | | | |
|---|---|---|---|
| 5,695,468 | A | 12/1997 | Lafontaine et al. |
| 5,709,703 | A | 1/1998 | Lukic et al. |
| 5,776,141 | A | 7/1998 | Klein et al. |
| 5,817,101 | A | 10/1998 | Fiedler |
| 5,989,263 | A | 11/1999 | Shmulewitz |
| 6,056,759 | A | 5/2000 | Fiedler |
| 6,059,813 | A | 5/2000 | Vrba et al. |
| 6,113,608 | A | 9/2000 | Monroe et al. |
| 6,214,037 | B1 | 4/2001 | Mitchell et al. |
| 6,287,285 | B1 | 9/2001 | Michal et al. |
| 6,425,898 | B1 | 7/2002 | Wilson et al. |
| 6,514,261 | B1 | 2/2003 | Randall et al. |
| 6,520,983 | B1 | 2/2003 | Colgan et al. |
| 6,541,116 | B2 | 4/2003 | Michal et al. |
| 6,605,109 | B2 | 8/2003 | Fiedler |
| 6,884,257 | B1 | 4/2005 | Cox |
| 6,942,682 | B2 | 9/2005 | Vrba et al. |
| 6,945,989 | B1 | 9/2005 | Betelia et al. |
| 7,163,552 | B2 | 1/2007 | Diaz |
| 7,632,296 | B2 | 12/2009 | Malewicz |
| 7,740,652 | B2 | 6/2010 | Gerdts et al. |
| 7,799,065 | B2 | 9/2010 | Pappas |
| 7,875,067 | B2 | 1/2011 | Von Oepen |
| 8,118,853 | B2 | 2/2012 | Grewe |
| 8,435,279 | B2 | 5/2013 | Beyerlein et al. |
| 8,652,198 | B2* | 2/2014 | Andreas ............ A61B 17/12022 623/1.16 |
| 8,685,076 | B2 | 4/2014 | Gerdts et al. |
| 9,119,742 | B2 | 9/2015 | Chuter et al. |
| 9,283,101 | B2 | 3/2016 | Shumer et al. |
| 9,326,875 | B2 | 5/2016 | Shumer et al. |
| 2001/0027323 | A1 | 10/2001 | Sullivan, III et al. |
| 2001/0044630 | A1* | 11/2001 | Stack .................... A61F 2/958 606/108 |
| 2002/0009535 | A1 | 1/2002 | Michal et al. |
| 2002/0010420 | A1 | 1/2002 | Bagaoisan et al. |
| 2002/0026182 | A1 | 2/2002 | Joye et al. |
| 2002/0045929 | A1 | 4/2002 | Diaz |
| 2002/0058951 | A1 | 5/2002 | Fiedler |
| 2002/0133118 | A1 | 9/2002 | Gerdts et al. |
| 2002/0165574 | A1 | 11/2002 | Ressemann et al. |
| 2003/0176910 | A1 | 9/2003 | Vrba et al. |
| 2003/0187474 | A1* | 10/2003 | Keegan ................ A61F 2/0095 606/200 |
| 2004/0143315 | A1 | 7/2004 | Bruun et al. |
| 2004/0193178 | A1 | 9/2004 | Nikolchev |
| 2004/0193243 | A1 | 9/2004 | Mangiardi et al. |
| 2005/0149166 | A1* | 7/2005 | Schaeffer ................ A61F 2/07 623/1.13 |
| 2005/0209674 | A1* | 9/2005 | Kutscher ............. A61B 17/22 623/1.11 |
| 2005/0222557 | A1 | 10/2005 | Baxter et al. |
| 2005/0278011 | A1* | 12/2005 | Peckham ................ A61F 2/958 623/1.11 |
| 2006/0030923 | A1 | 2/2006 | Gunderson |
| 2006/0106366 | A1 | 5/2006 | Wang |
| 2006/0200191 | A1 | 9/2006 | Zadno-azizi |
| 2006/0200221 | A1 | 9/2006 | Malewicz |
| 2007/0078506 | A1 | 4/2007 | McCormick et al. |
| 2007/0083188 | A1 | 4/2007 | Grandt et al. |
| 2007/0100413 | A1 | 5/2007 | Dwyer et al. |
| 2007/0123971 | A1 | 5/2007 | Kennedy et al. |
| 2008/0118544 | A1* | 5/2008 | Wang .................. A61K 31/337 424/423 |
| 2008/0125711 | A1 | 5/2008 | Alpini et al. |
| 2008/0294230 | A1 | 11/2008 | Parker |
| 2009/0018529 | A1 | 1/2009 | Hoffman et al. |
| 2009/0204197 | A1 | 8/2009 | Dorn et al. |
| 2009/0292262 | A1 | 11/2009 | Adams et al. |
| 2009/0312832 | A1 | 12/2009 | Delap |
| 2010/0087906 | A1 | 4/2010 | Dorn et al. |
| 2010/0286756 | A1 | 11/2010 | Dorn et al. |
| 2011/0112567 | A1 | 5/2011 | Lenker et al. |
| 2011/0307049 | A1 | 12/2011 | Kao |
| 2012/0148175 | A1 | 6/2012 | Wesselmann |
| 2013/0073024 | A1 | 3/2013 | Russo et al. |
| 2013/0138090 | A1 | 5/2013 | Fargahi |
| 2013/0297011 | A1 | 11/2013 | Morris et al. |
| 2013/0304179 | A1 | 11/2013 | Bialas et al. |
| 2013/0304180 | A1* | 11/2013 | Green .................... A61F 2/966 623/1.11 |
| 2013/0304181 | A1 | 11/2013 | Green et al. |
| 2014/0194969 | A1 | 7/2014 | Headley |
| 2014/0214151 | A1 | 7/2014 | Ibeling |
| 2014/0277356 | A1 | 9/2014 | Shumer et al. |

OTHER PUBLICATIONS

U.S. Appl. No. 13/467,679, May 11, 2016 Response to Non-Final Office Action.
U.S. Appl. No. 14/643,110 (US 2015/0245937), filed Mar. 10, 2015 (Sep. 3, 2015).
U.S. Appl. No. 15/163,984, filed May 25, 2016.
U.S. Appl. No. 14/643,110, May 27, 2016 Issue Fee Payment.
U.S. Appl. No. 14/643,110, Feb. 29, 2016 Notice of Allowance.
U.S. Appl. No. 14/643,110, Oct. 30, 2015 Response to Non-Final Office Action.
U.S. Appl. No. 14/643,110, Jul. 30, 2015 Non-Final Office Action.
U.S. Appl. No. 13/467,679, Feb. 11, 2016 Non-Final Office Action.
U.S. Appl. No. 13/467,679, Oct. 14, 2014 Response to Restriction Requirement.
U.S. Appl. No. 13/467,715, Jan. 20, 2016 Issue Fee Payment.
U.S. Appl. No. 13/467,715, Dec. 18, 2015 Notice of Allowance.
U.S. Appl. No. 13/467,715, Nov. 9, 2015 Response to Restriction Requirement.
U.S. Appl. No. 13/467,715, Sep. 9, 2015 Restriction Requirement Filed.
U.S. Appl. No. 13/797,636, Feb. 5, 2016 Issue Fee Payment.
U.S. Appl. No. 13/801,588, Mar. 31, 2016 Issue Fee Payment.
U.S. Appl. No. 13/801,588, Feb. 1, 2016 Notice of Allowance.
U.S. Appl. No. 13/801,588, Jan. 22, 2016 Applicant Initiated Interview Summary.
U.S. Appl. No. 13/801,588, Nov. 19, 2015 Response to Non-Final Office Action.
U.S. Appl. No. 13/801,588 (US 2014/0276412), filed Mar. 13, 2013 (Sep. 18, 2014).
U.S. Appl. No. 13/797,636 (US 2014/0277356), filed Mar. 12, 2013 (Sep. 18, 2014).
U.S. Appl. No. 13/467,660 (U.S. Pat. No. 9,011,513), filed May 9, 2012 (Apr. 21, 2015).
U.S. Appl. No. 13/467,679 (US 2013/0304180), filed May 9, 2012 (Nov. 14, 2013).
U.S. Appl. No. 13/467,715 (US 2013/0304181), filed May 9, 2012 (Nov. 14, 2013).
U.S. Appl. No. 14/653,582, filed Jun. 18, 2015.
U.S. Appl. No. 13/467,660, Oct. 7, 2013 Non-Final Office Action.
U.S. Appl. No. 13/467,660, Jan. 7, 2014 Response to Non-Final Office Action.
U.S. Appl. No. 13/467,660, Jul. 17, 2014 Final Office Action.
U.S. Appl. No. 13/467,660, Oct. 14, 2014 Response after Final Action.

(56) References Cited

OTHER PUBLICATIONS

U.S. Appl. No. 13/467,660, Nov. 25, 2014 Notice of Allowance.
U.S. Appl. No. 13/467,660, Feb. 25, 2015 Issue Fee Payment.
U.S. Appl. No. 13/467,679, Aug. 22, 2014 Restriction Requirement.
U.S. Appl. No. 13/801,588, Jul. 9, 2015 Restriction Requirement Filed.
U.S. Appl. No. 13/801,588, Aug. 20, 2015 Non-Final Office Action.
U.S. Appl. No. 13/797,636, Jun. 30, 2015 Non-Final Office Action.
International Search Report and Written Opinion for PCT/US2013/036881, dated Aug. 2, 2013.
International Search Report and Written Opinion for PCT/US2013/036884, dated Aug. 2, 2013.
International Search Report and Written Opinion for PCT/US2013/030513, dated Aug. 2, 2013.
International Search Report for PCT/US2013/068306, dated Jan. 8, 2014.
International Search Report for PCT/US2013/030830, dated Jan. 15, 2014.
International Search Report and Written Opinion for PCT/US2013/069477, dated Jan. 8, 2014.
U.S. Appl. No. 13/467,679, Aug. 25, 2017 Notice of Abandonment.
U.S. Appl. No. 13/467,679, Apr. 24, 2017 Applicant Initiated Interview Summary.
U.S. Appl. No. 13/467,679, Feb. 9, 2017 Final Office Action.
U.S. Appl. No. 13/467,679, Nov. 22, 2016 Amendment and Request for Continued Examination (RCE).
U.S. Appl. No. 13/467,679, Aug. 22, 2016 Final Office Action.
U.S. Appl. No. 14/653,582, Nov. 14, 2017 Non-Final Office Action.
U.S. Appl. No. 14/653,582, Oct. 6, 2017 Response to Restriction Requirement.
U.S. Appl. No. 14/653,582, Aug. 14, 2017 Restriction Requirement.
U.S. Appl. No. 15/180,655, Jan. 17, 2018 Notice of Allowance.
U.S. Appl. No. 15/180,655, Sep. 5, 2017 Response to Non-Final Office Action.
U.S. Appl. No. 15/180,655, May 2, 2017 Non-Final Office Action.
U.S. Appl. No. 15/016,520 (US 2016/0151185), filed Feb. 5, 2016 (Jun. 2, 2016).
U.S. Appl. No. 15/016,520, May 16, 2018 Non-Final Office Action.
U.S. Appl. No. 15/163,984, Jun. 22, 2018 Non-Final Office Action.
U.S. Appl. No. 15/163,984, Feb. 15, 2019 Final Office Action.
CN Office Action dated Jun. 30, 2015 in CN Patent Application No. 201380007953.4.
U.S. Appl. No. 13/797,636, Dec. 10, 2015 Notice of Allowance.

* cited by examiner

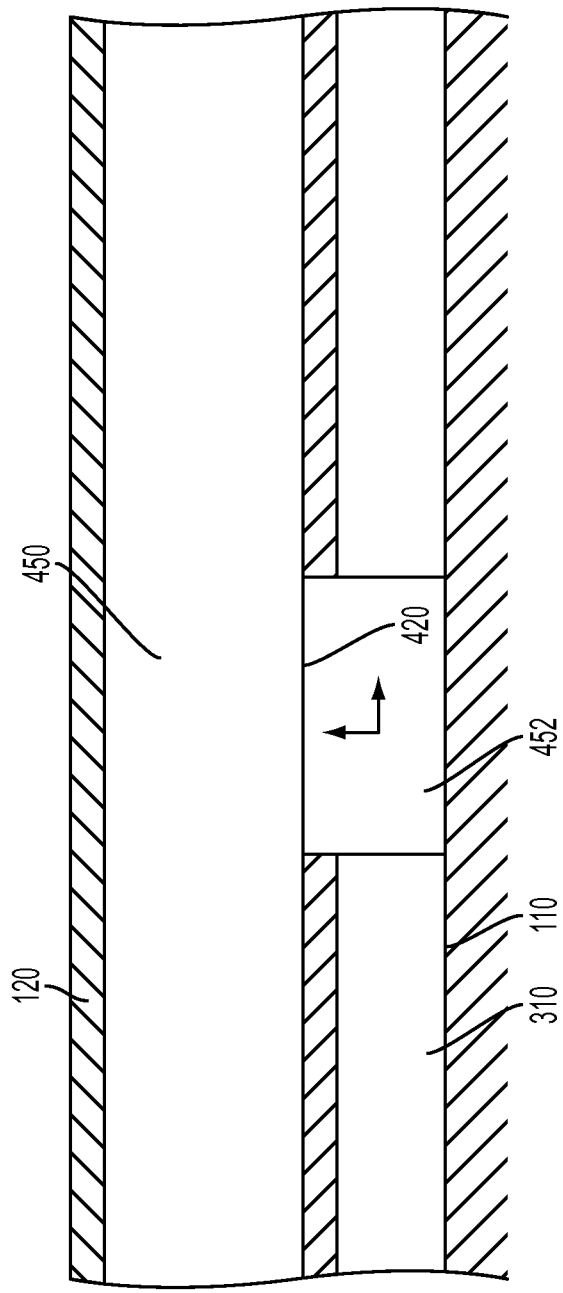

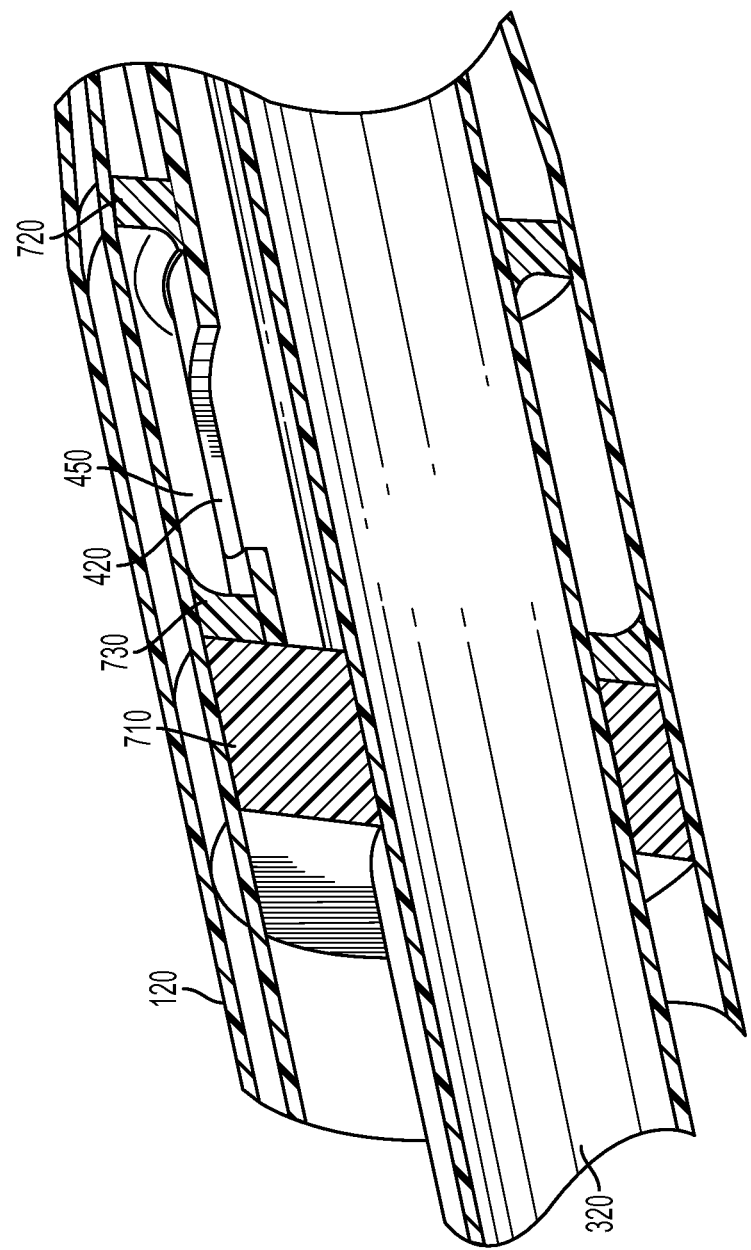

BALLOON CATHETER HAVING HYDRAULIC ACTUATOR

CROSS-REFERENCE TO RELATED APPLICATION

This application is a U.S. National Stage Patent Application under 35 U.S.C. § 371 of International Application No. PCT/US2013/069477, filed on Nov. 11, 2013, which is a continuation-in-part of and claims priority to U.S. application Ser. No. 13/801,588, entitled "Catheter Having Movable Tubular Structure" and filed on Mar. 13, 2013, and is a continuation-in-part of and claims priority to U.S. application Ser. No. 13/797,636, entitled "Catheter Having Hydraulic Actuator and Locking System" and filed on Mar. 12, 2013, the disclosure of each of which is incorporated herein by reference in its entirety.

BACKGROUND OF THE DISCLOSED SUBJECT MATTER

Field of the Disclosed Subject Matter

The disclosed subject matter relates to catheters used in the delivery of medical devices such as expandable members, self-expanding stents, and stents delivered by an expandable member for treating the luminal systems of a patient. Specifically, the disclosed subject matter relates to a delivery catheter having a retractable sheath moved by a hydraulic actuator.

Description of the Related Art

In general, catheters such as balloon catheters, can be used for a variety of suitable procedures and treatments. Such procedures include, but are not limited to, procedures for dilatation, delivery of medical devices such as stents, stent grafts, filters, and the like, and procedures for drug delivery. As known in the art, a variety of catheter devices treat the luminal system of a patient. Of such devices, many are directed to treating vascular systems, including both the cardiovascular system and the peripheral system of a patient. For example, the treatment of the cardiovascular system can include the performance of angioplasty or delivery of balloon-expandable or self-expanding interventional devices (e.g., stents). The treatment of the peripheral system includes treatment of the carotid, popliteal and renal vessels, among others.

The site of the occlusive lesion can often only be reached by a tortuous pathway through the vasculature of the patient. The difficulty in accessing such regions requires that the catheter must be sufficiently flexible longitudinally to follow the tortuous path to the desired site, and at the same time, sufficiently stiff axially to allow the distal end of the catheter to be pushed or otherwise manipulated from an external access location. In manipulating the catheter through the tortuous pathway, the catheter furthermore needs sufficient structure to maintain the patency of the balloon and/or any medical device delivered by the catheter, including preventing drugs or therapeutic agents from being released prematurely from the catheter prior to deployment.

A variety of systems using a retractable sheath are known for intraluminal delivery of a medical device, such as an expandable member, stent, stent graft, or filter. However, there remains a need for continued improvement of such known delivery systems.

An example of such a system is described in U.S. Pat. No. 6,425,898 to Wilson et al., which is incorporated by reference herein, wherein a delivery system is provided having an inner member with a stop attached to the inner member. During deployment, the stop prevents the stent from migrating proximally during retraction of the sheath for stent deployment.

Conventional medical device delivery systems generally comprise a handle portion and an elongated shaft, wherein a medical device such as an expandable member disposed at the distal end of the shaft. In certain embodiments, a retractable sheath can also be provided and initially disposed over the expandable member. To deploy the device, the outer sheath can be retracted relative to the expandable member, which can then be inflated to a deployed configuration. The sheath in such systems generally spans the full length of the catheter resulting in an increased profile and stiffness over the entire length of the catheter. Such stiffness and increased profile at the distal end of the catheter can restrict certain applications, such as neuro and other indications of particular size limitations. Further, because the sheath spans the full length of the catheter there is an increased risk of the sheath binding with other components of the catheter during passage through the tortuous luminal system of a patient, thus inhibiting the deployment of the stent.

Another issue with such delivery systems is that the sheath is generally pulled back in a 1-to-1 ratio with the user's input (force). Due to larger static friction forces, a large amount of initial input may be typically required to retract the sheath.

Further, the amount of force that is required to retract the sheath, particularly for balloons or stents of greater length as required for peripheral indications, can be substantial. To overcome this issue, a lubricious liner can be used to decrease the amount of force required to retract the sheath. However, there remains a need for an improved delivery system with a retractable sheath having reduced force requirements for delivery of the medical device.

There thus remains a continued need for an efficient and economic system for delivering a medical device that is easy to use and provides accurate placement. The presently disclosed subject matter satisfies these and other needs.

SUMMARY OF THE DISCLOSED SUBJECT MATTER

The purpose and advantages of the disclosed subject matter will be set forth in and are apparent from the description that follows, as well as will be learned by practice of the disclosed subject matter. Additional advantages of the disclosed subject matter will be realized and attained by the devices particularly pointed out in the written description and claims hereof, as well as from the appended drawings.

To achieve these and other advantages and in accordance with the purpose of the disclosed subject matter, as embodied and broadly described, the disclosed subject matter includes a catheter comprising, among other things, an inner tubular member having a proximal end portion, a distal end portion and an exterior surface, the inner tubular member further having a fluid lumen and an inflation lumen defined therein, the fluid lumen having a fluid flow port defined by the exterior surface along the distal end portion of the inner tubular member; an outer tubular member movable relative to the inner tubular member, the outer tubular member having a proximal end, a distal end and an interior surface directed toward the exterior surface of the inner tubular member; an expandable member coupled to the distal end portion of the inner tubular member and having an inner chamber in fluid communication with the inflation lumen, the expandable member transitionable between a deflated configuration and an inflated configuration; a proximal seal extending from the interior surface of the outer tubular member toward the exterior surface of the inner tubular member, the proximal seal located proximal to the fluid flow port; a distal seal extending from the exterior surface of the inner tubular member toward the interior surface of the outer tubular member, the distal seal located distal to the fluid flow port; and a pressure chamber defined by the proximal seal, the distal seal, the exterior surface of the inner tubular member and interior surface of the outer tubular member, with the pressure chamber in fluid communication with the fluid flow port, wherein fluid introduced through the fluid flow port and into the pressure chamber applies a force on the proximal seal to urge the outer tubular member in a proximal direction.

In accordance with another aspect of the disclosed subject matter, as embodied and broadly described, the disclosed subject matter includes a catheter comprising, among other things, an inner tubular member having a proximal end portion, a distal end portion and an exterior surface, the inner tubular member further having a fluid lumen defined therein, the fluid lumen having a fluid flow port defined by the exterior surface along the distal end portion of the inner tubular member, the fluid lumen further including a directional control valve fluidly coupled with the fluid flow port, the directional control valve having a first position and a second position; an outer tubular member movable relative to the inner tubular member, the outer tubular member having a proximal end, a distal end and an interior surface directed toward the exterior surface of the inner tubular member; an expandable member coupled to the distal end portion of the inner tubular member and having an inner chamber in fluid communication with the fluid lumen, the expandable member transitionable between a deflated configuration and an inflated configuration; a proximal seal extending from the interior surface of the outer tubular member toward the exterior surface of the inner tubular member, the proximal seal located proximal to the fluid flow port; a distal seal extending from the exterior surface of the inner tubular member toward the interior surface of the outer tubular member, the distal seal located distal to the fluid flow port; and a pressure chamber defined by the proximal seal, the distal seal, the exterior surface of the inner tubular member and interior surface of the outer tubular member, with the pressure chamber in fluid communication with the fluid flow port, wherein the directional control valve in the first position directs fluid introduced in the fluid lumen through the fluid flow port into the pressure chamber to apply a force on the proximal seal to urge the outer tubular member in a proximal direction and wherein the directional control valve in the second position directs fluid through the fluid lumen into the inner chamber of the expandable member to inflate the expandable member to the inflated configuration.

It is to be understood that both the foregoing general description and the following detailed description and drawings are examples and are provided for purpose of illustration and not intended to limit the scope of the disclosed subject matter in any manner.

The accompanying drawings, which are incorporated in and constitute part of this specification, are included to illustrate and provide a further understanding of the devices of the disclosed subject matter. Together with the description, the drawings serve to explain the principles of the disclosed subject matter.

BRIEF DESCRIPTION OF THE DRAWINGS

The subject matter of the application will be more readily understood from the following detailed description when read in conjunction with the accompanying drawings, in which:

FIG. 4A is a cross sectional detail side view of the pressure chamber and directional control valve of a catheter in accordance with the disclosed subject matter.

FIG. 11 is a cross sectional perspective view of the detail of FIG. 10.

DETAILED DESCRIPTION

Figure 1:
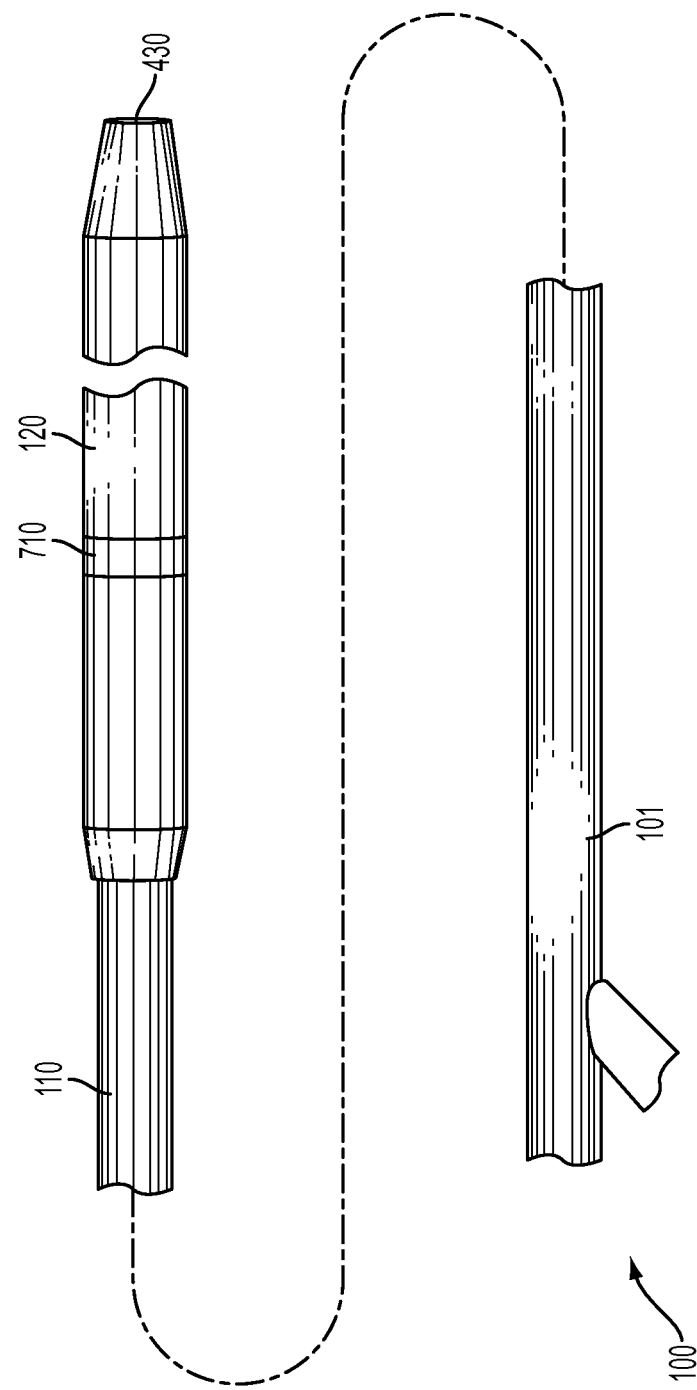
FIG. 1 is a schematic side view of a representative catheter in accordance with the disclosed subject matter.

Reference will now be made in detail to embodiments of the disclosed subject matter, an example of which is illustrated in the accompanying drawings. The disclosed subject matter will be described in conjunction with the detailed description of the system.

As disclosed herein, the devices presented herein can be used for treating the luminal system of a patient. The disclosed subject matter is particularly suited for treatment of the cardiovascular system and the peripheral system of a patient. The treatment of the cardiovascular system includes the performance of angioplasty or delivery of balloon-expandable or self-expanding interventional devices (e.g., stents, stent grafts, filters, coils). The treatment of the peripheral system includes, but is not limited to, treatment of the carotid, popliteal and renal vessels. Accordingly, the present disclosed subject matter is also suitable for a variety of particular endovascular vessels.

With treatment of the peripheral system, catheters according to embodiments of the disclosed subject matter can further be used in vessels with multiple lesions, such as, but not limited to, below the knee vessels. Thus, the catheter according to an embodiment of the disclosed subject matter is not limited to a single long, short, diffuse, or focal lesion. The catheter can treat any combination lesions due to the ability of the catheter to adapt to specific lesion or combination of lesions.

In accordance with the disclosed subject matter, a catheter is provided comprising, among other things, an inner tubular member having a proximal end portion, a distal end portion and an exterior surface, the inner tubular member further having a fluid lumen and an inflation lumen defined therein, the fluid lumen having a fluid flow port defined by the exterior surface along the distal end portion of the inner tubular member; an outer tubular member movable relative to the inner tubular member, the outer tubular member having a proximal end, a distal end and an interior surface directed toward the exterior surface of the inner tubular member; an expandable member coupled to the distal end portion of the inner tubular member and having an inner chamber in fluid communication with the inflation lumen, the expandable member transitionable between a deflated configuration and an inflated configuration; a proximal seal extending from the interior surface of the outer tubular member toward the exterior surface of the inner tubular member, the proximal seal located proximal to the fluid flow port; a distal seal extending from the exterior surface of the inner tubular member toward the interior surface of the outer tubular member, the distal seal located distal to the fluid flow port; and a pressure chamber defined by the proximal seal, the distal seal, the exterior surface of the inner tubular member and interior surface of the outer tubular member, with the pressure chamber in fluid communication with the fluid flow port, wherein fluid introduced through the fluid flow port and into the pressure chamber applies a force on the proximal seal to urge the outer tubular member in a proximal direction.

Figure 2:
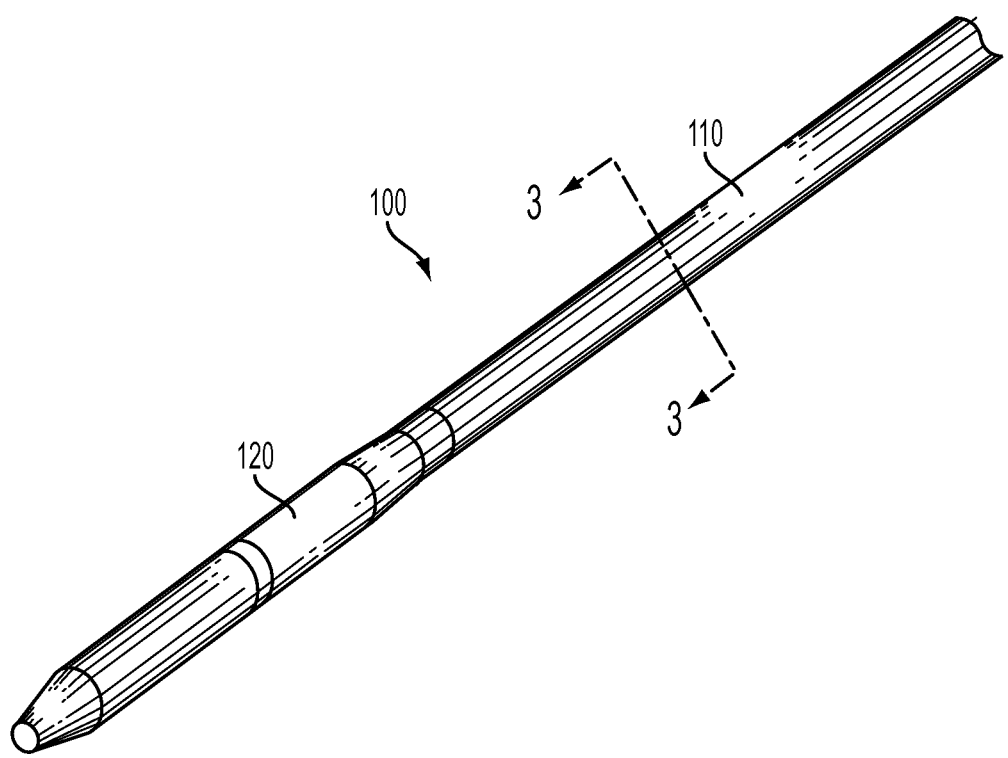
FIG. 2 is a perspective view of the distal end section of the catheter of FIG. 1.

Solely for purpose of illustration, an exemplary embodiment of a hydraulic delivery system for a medical device, is shown schematically in FIGS. 1 and 2. The examples herein are not intended to limit the scope of the disclosed subject matter in any manner. Particularly, and as illustrated, the hydraulic delivery system embodied herein is a catheter 100 for cardiovascular intervention or the like. Catheters for other interventions, such as peripheral and below the knee interventions, are contemplated herein.

The catheter 100 includes an inner tubular member 110 having a proximal end portion, a distal end portion, and an exterior surface. The catheter 100 further includes an outer tubular member or sheath 120 which is movable relative to the inner tubular member 110 and has a proximal end, a distal end and an interior surface directed toward the exterior surface of the inner tubular member 110. As shown in FIG. 2, the outer tubular member 120 is disposed only at a distal end portion of the catheter in this embodiment. For other embodiments, the outer tubular member 120 can be disposed at the proximal end portion and/or the distal end portion of the catheter. As described further herein, the catheter of the disclosed subject matter can be configured to deliver a medical device to a desired site within the body. Such medical devices can include an expandable member or members, such as a balloon(s), an embolic filter, stent graft, and/or a stent(s). That is, the catheter can be configured to generate a force sufficient to retract the outer tubular member, wherein the generated force is greater than the resistance force caused by the medical device acting on the outer tubular member.

Figure 3A:
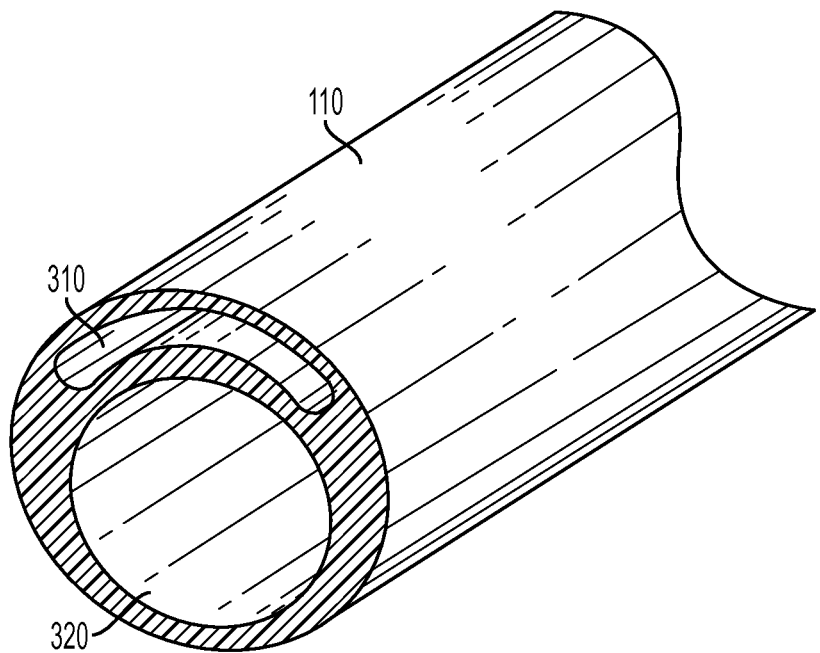
FIG. 3A is a cross sectional perspective view of the catheter of FIG. 2 taken along line 3-3.

Solely for purpose of illustration, reference is made to FIG. 3A which depicts a representative cross sectional view of an exemplary inner tubular member 110 along lines 3-3 of FIG. 2, in accordance with the disclosed subject matter. The inner tubular member 110 further has a fluid lumen 310 defined therein. In certain embodiments, the inner tubular member can also have a guidewire lumen 320 defined at least along a length therein. For example, the guidewire lumen 320, if provided, can extend over the entire length of the inner tubular member 110 such as for an "over-the-wire" configuration, or only along a distal length such as for a "rapid exchange" embodiment. Alternatively the catheter 100 can have a single-lumen design and the guidewire and pressurized fluid can share the same lumen (not shown), wherein a seal or valve can be provided at distal and proximal ends.

Figure 3B:
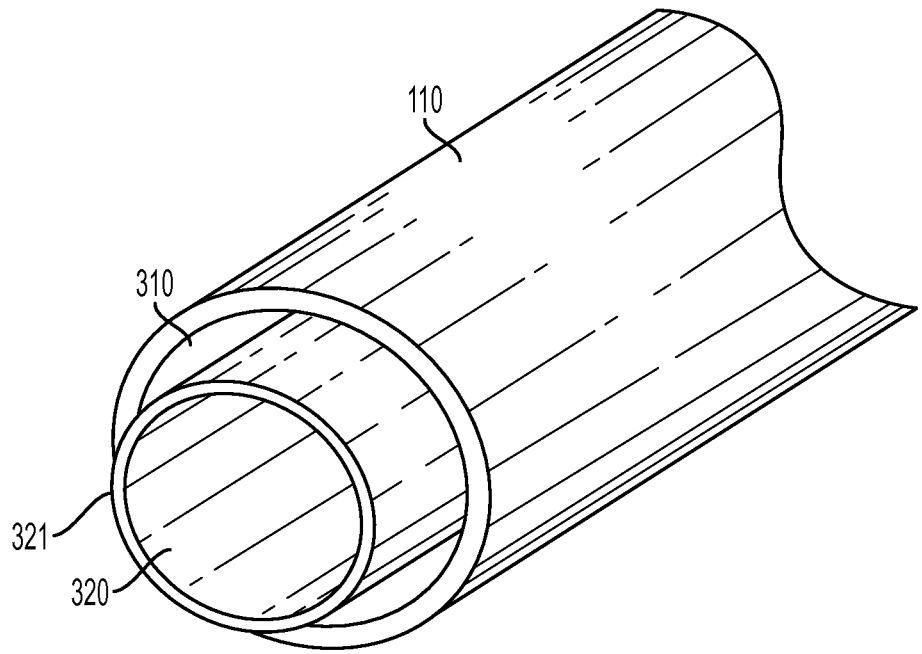
FIG. 3B is a cross sectional perspective view of another embodiment of the catheter of FIG. 2 taken along line 3-3.

FIG. 3B depicts another embodiment of a representative cross sectional view of an exemplary inner tubular member 110 along lines 3-3 of FIG. 2. In this embodiment, as shown in FIG. 3B solely for purposes of illustration, the guidewire lumen 320 can be defined at least in part by a separate guidewire tube 321 disposed within a fluid lumen 310 and sealed at either side, such as for example, by a marker (not shown). Such coaxial configurations allow for reduced diameter of the inner tubular member 110, and thus reduced profile. Indeed the guidewire tube 321 defining the guidewire lumen 320 can be formed by a thin membrane of suitable strength to prevent the guidewire from penetrating therethrough. Hydraulic fluid can thus flow within the fluid lumen 310 but outside the guidewire lumen 320.

When the medical device includes an expandable member, the expandable member generally will be coupled to the distal end portion of the inner tubular member and have an inner chamber defined therein. Additionally, a lumen will be required to direct inflation medium into/out of the inner chamber of the expandable member. Presently, catheter balloon materials generally can be classified as compliant, semi-compliant, or non-compliant balloons. Compliance can be defined as the increase in the balloon diameter above nominal balloon pressure. Generally, non-compliant balloons have less increase in diameter than semi-compliant balloons, which in turn have less increase in diameter than compliant balloons.

Compliant balloons expand and stretch with increasing pressure within the balloon, and are made from such materials as silicone, thermoplastic elastomers (TPEs), and polyethylene or polyolefin copolymers. Non-compliant balloons, made from such materials as polyethylene terephthalate (PET) or polyamides, remain substantially at a pre-selected diameter as the internal balloon pressure increases beyond that required to fully inflate the balloon. However, noncompliant balloons generally have relatively low flexibility and softness, so that it has been difficult to provide a low compliant balloon with high flexibility and softness for enhanced catheter trackability. A balance is typically struck between the competing considerations of softness/flexibility and noncompliance, which, as a result, has limited the degree to which the compliance of catheter balloons can be further lowered.

Figure 3C:
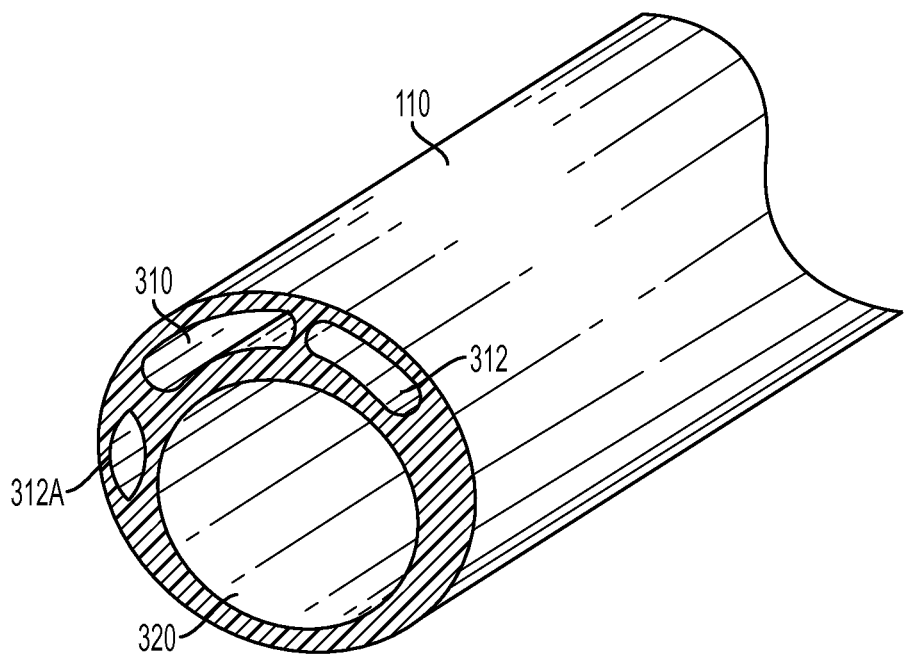
FIG. 3C is a cross sectional perspective view of another embodiment of the catheter of FIG. 2 taken along line 3-3.

FIG. 3C depicts another embodiment of a representative cross sectional view of an exemplary inner tubular member 110 along lines 3-3 of FIG. 2. In this embodiment, as shown in FIG. 3C solely for purposes of illustration, the inner tubular member additionally includes an inflation lumen 312. The inflation lumen 312 can extend along the catheter substantially parallel to the fluid lumen 310 and/or the guidewire lumen 320. The inflation lumen, if provided, is in fluid communication with the inner chamber 541 of the expandable member 540, as described further below. Fluid can be introduced into the inflation lumen 312 at a proximal end of the catheter 100 via luer adapter 101 or the like. The inflation lumen 312 thus directs an inflation medium under positive pressure to the inner chamber and likewise can facilitate withdrawal of the inflation medium, e.g., by negative pressure, from the expandable member. The expandable member 540 can thus be inflated and deflated by the inflation lumen, as further discussed below. In other embodiments and in lieu of a separate inflation lumen, the fluid lumen 310 can be fluidly coupled to the inner chamber 541 of the expandable member 540, as further discussed herein.

Figure 3D:
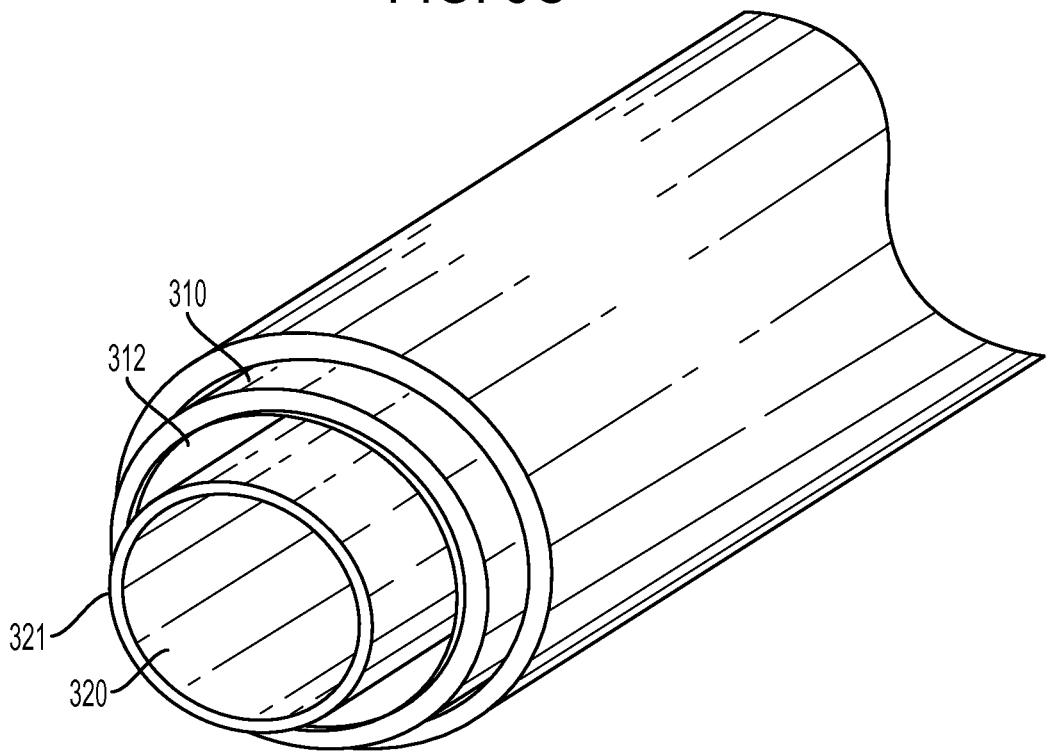
FIG. 3D is a cross sectional perspective view of another embodiment of the catheter of FIG. 2 taken along line 3-3.

For embodiments having one or more expandable members, additional inflation lumens can be provided. FIG. 3C shows a second inflation lumen 312A that supplies inflation medium to a second expandable member (not shown), as further discussed herein. In other embodiments as shown in FIG. 3D, the inflation lumen 312 can be coaxial with the guidewire lumen 320 and the fluid lumen 310.

Figure 4:
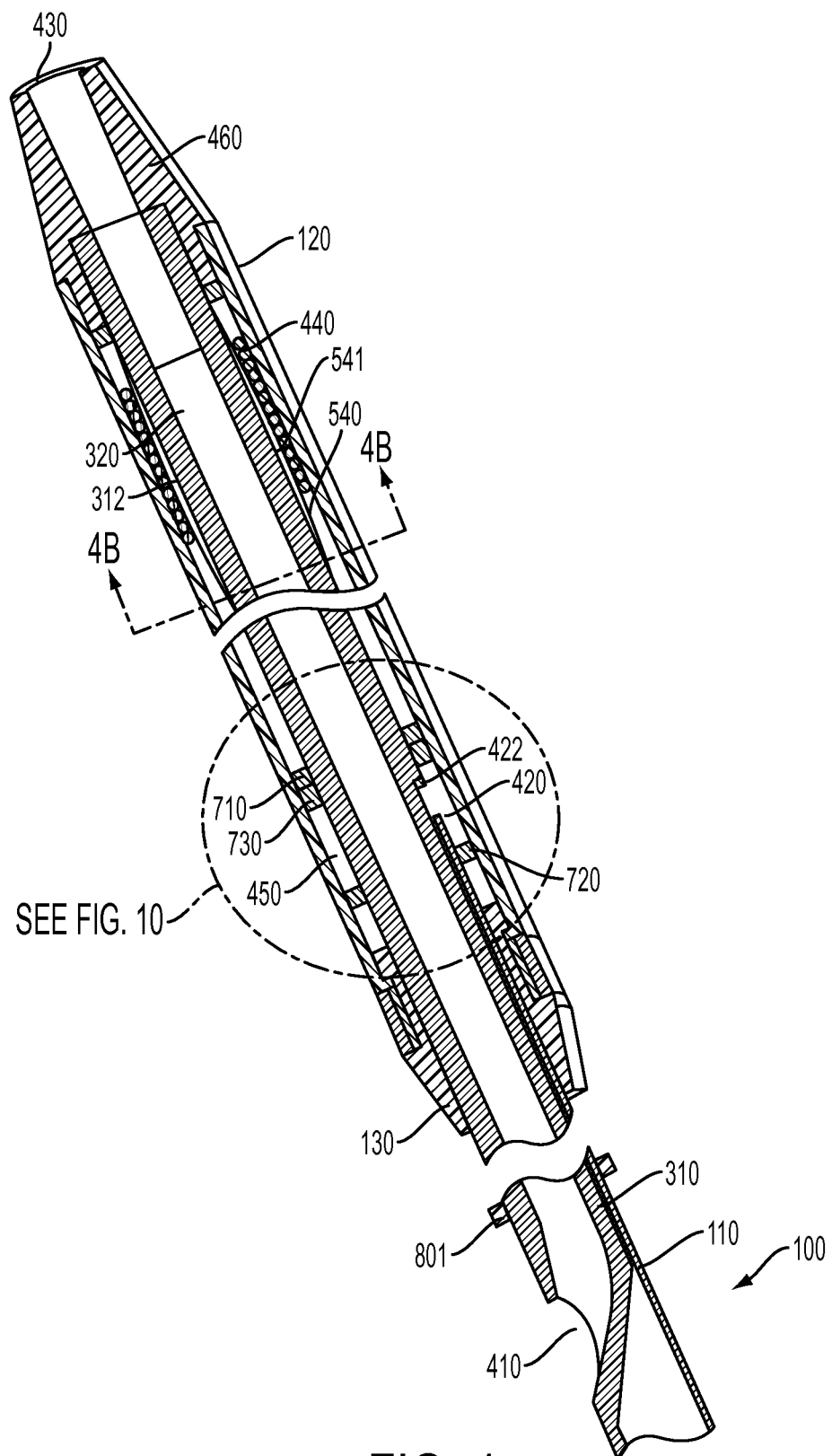
FIG. 4 is a cross sectional perspective side view of the distal end section of a catheter in accordance with the disclosed subject matter with the sheath in a closed position.

Solely for purpose of illustration, reference is now made to a rapid exchange configuration of a balloon catheter disclosed herein as shown in FIG. 4. Generally, the catheter includes an inner tubular member 110 having a proximal end portion, a distal end portion and an exterior surface. The inner tubular member 110 further includes a fluid lumen 310 having a fluid flow port 420 defined by the exterior surface 111 along a distal end portion of inner tubular member 110 and an inflation lumen (not shown) defined therein. The outer tubular member 120 is movable relative to the inner tubular member 110 and has a proximal end, a distal end and an interior surface 121 directed toward the exterior surface 111 of the inner tubular member 110. The expandable member 540 is coupled to the distal end portion of the inner tubular member 110 and has an inner chamber 541 in fluid communication with the inflation lumen 312. The expandable member is transitionable between a deflated configuration and an inflated configuration, as shown respectively in FIGS. 4 and 6 and further discussed herein.

As described in more detail below, the fluid flow port 420 allows fluid to pass from within fluid lumen 310 into the space defined by the inner tubular member 110 and outer tubular member 120 for operation and retraction of the outer tubular member 120. For balloon catheter embodiments without a separate inflation lumen, the fluid lumen 310 can introduce fluid to the expandable member 540. In such embodiments as shown in the detail FIG. 4A, the fluid flow port 420 additionally can include a directional control valve 452 having a first position to direct fluid introduced in the fluid lumen through the fluid flow port into the pressure chamber and a second position to direct fluid through the fluid lumen into the inner chamber of the expandable member to inflate the expandable member to the inflated configuration. A marker 422 can define the distal end of the fluid flow port 420. As embodied herein, the rapid exchange catheter further includes guidewire lumen 320 extending along a distal end portion of the catheter and including a proximal guidewire port 410 and a distal guidewire port 430.

Figure 6:
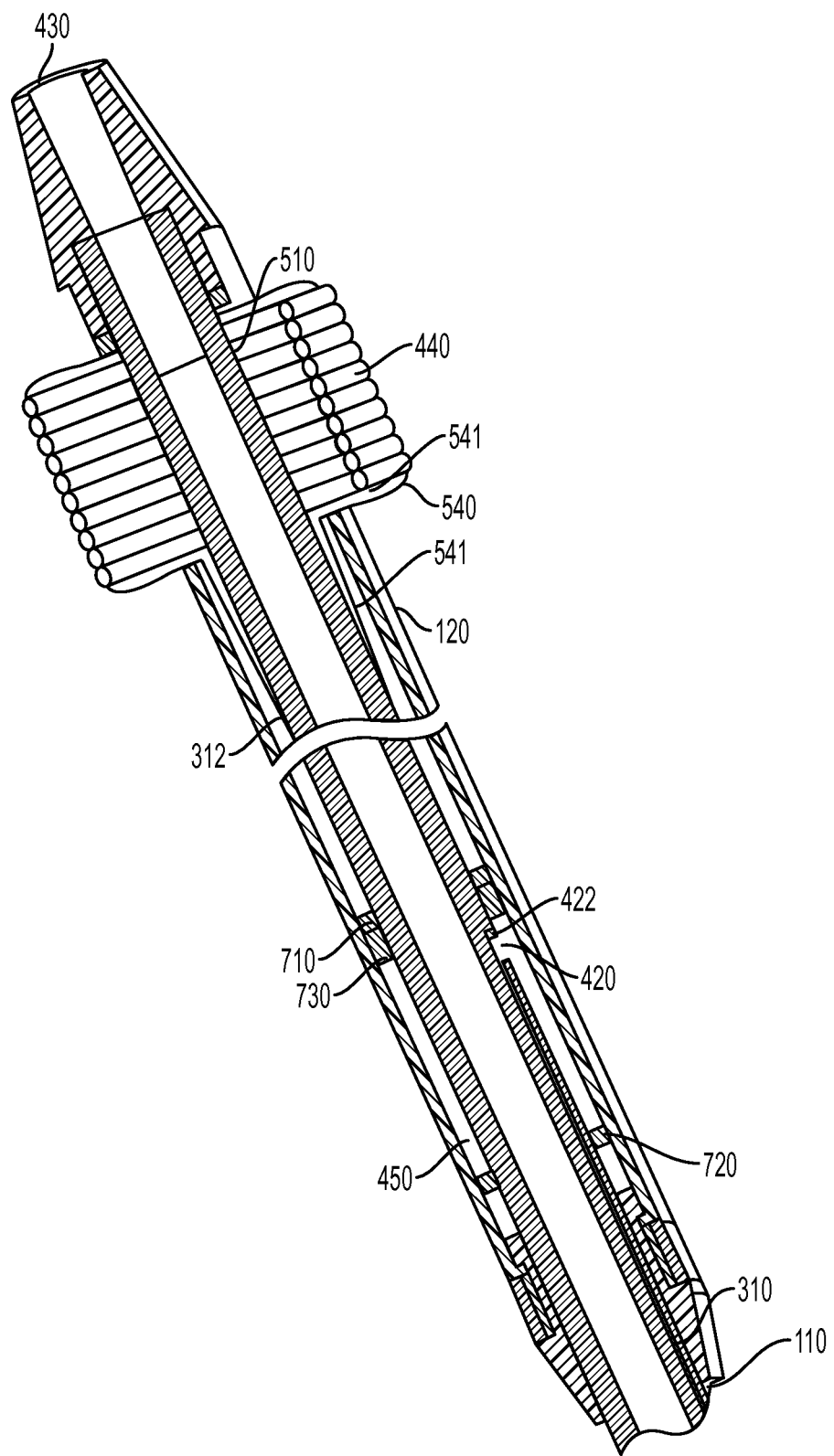
FIG. 6 is a cross sectional side view of the distal end of the catheter of FIG. 4 with the sheath in a fully retracted position.
Figures 7, 7A:
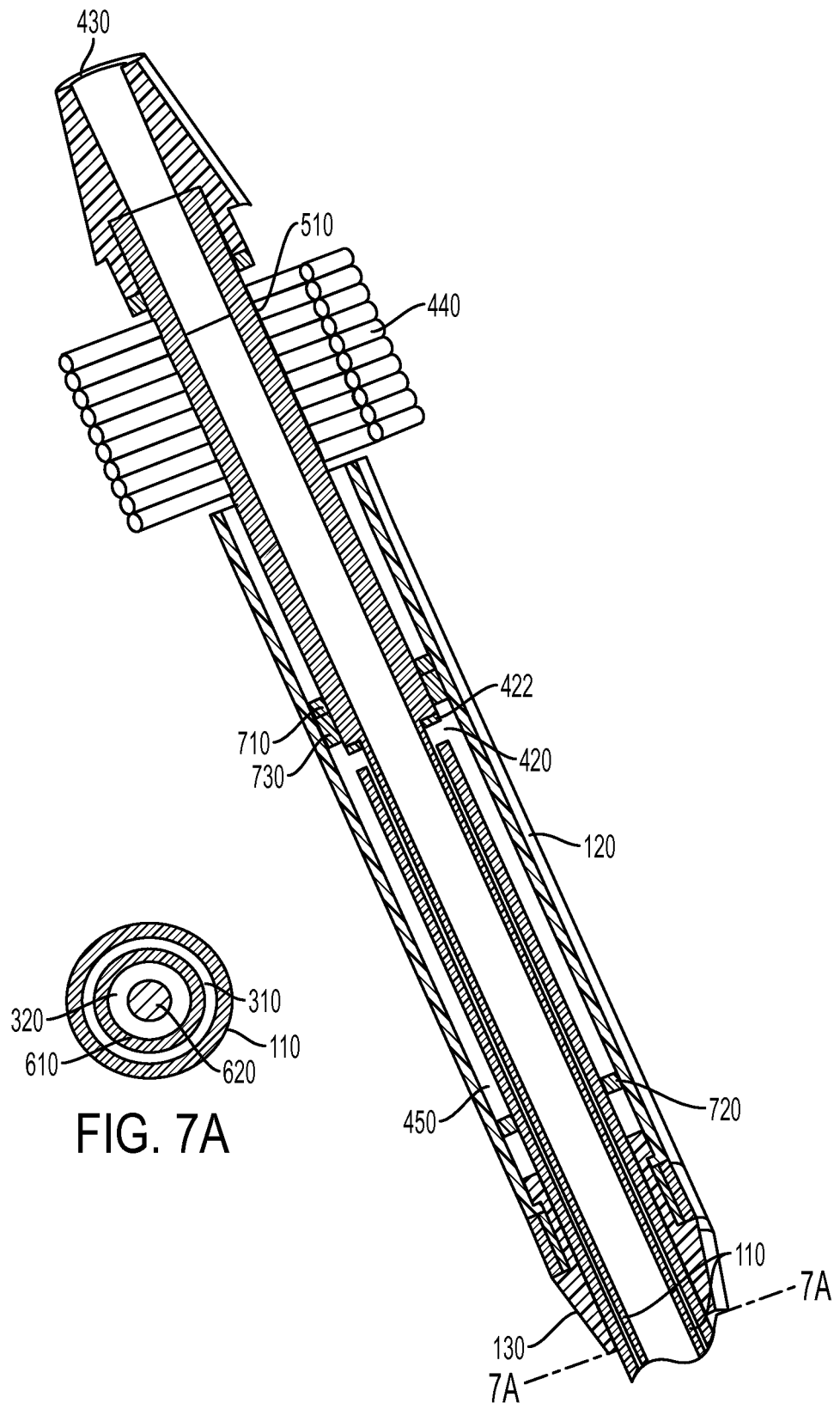
FIG. 7 is a cross sectional side view of the distal end section of an alternative catheter in accordance with the disclosed subject matter with the sheath in a fully retracted position.
FIG. 7A is a cross sectional view of the catheter of FIG. 7 taken at line 7A.

As illustrated, the outer tubular member 120 can be moved from an extended position as shown in FIG. 4 to a retracted position shown in FIG. 6. When extended, the outer tubular member 120 retains a medical device, such as the expandable member 540 and stent 440, if provided, as depicted herein, in a compressed or delivery condition. A distal tip 460 can also be provided at a distal end of the inner tubular member 110 to further enclose the medical device during delivery. When the outer tubular member 120 is retracted (as shown in FIGS. 6 and 7), the medical device is unsheathed, the balloon can be expanded, and the stent, when provided, can be allowed to expand to a deployed condition.

In accordance with the disclosed subject matter and as depicted in FIGS. 4-7, the outer tubular member 120 further includes at least one movable tubular structure 130 is disposed between the outer tubular member 120 and the inner tubular member 110. With reference to FIGS. 5A and 5B, a detailed view of the movable tubular structure 130 is provided, according to a representative embodiment of the subject matter. The movable tubular structure 130 generally comprises a body member 131 with an outer surface having a recess 134 defined therein. As further shown in FIG. 5A, and as embodied herein, the body member 131 includes a taper segment 132 and a base segment 133. FIG. 5A shown, for purposes of illustration, the recess 134 is disposed in the base segment 133 of the body member 131. Alternative embodiments of the disclosed subject matter likewise include one or more recesses in the taper segment 132 and/or one or more recesses in the base segment 133. For example, FIG. 5C depicts a movable tubular structure 130 having a recess 134 being disposed in the taper segment 132 of the body member 131 and additional recesses 134A and 134B being disposed in the base segment 133.

Figure 5A:
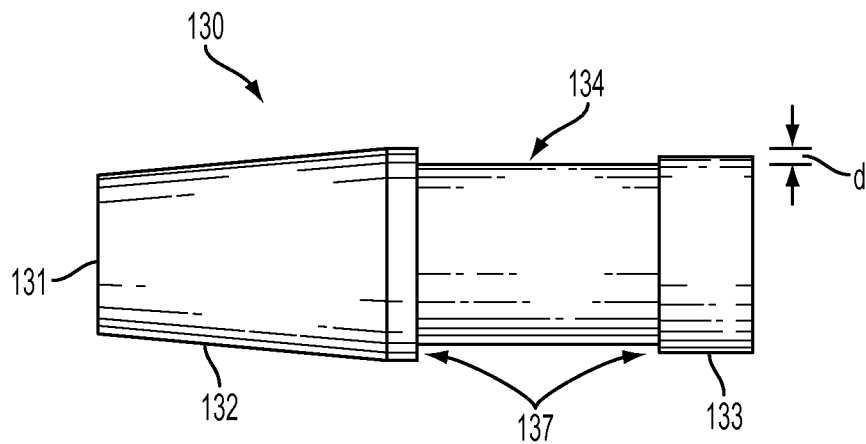
FIG. 5A is a detailed view of a movable tubular structure in accordance with a representative embodiment of the disclosed subject matter.

As disclosed herein, the recess 134 can be defined at least in part by at least one shoulder 137 proximate the outer surface to the body member 131. The shoulder 137 has an angle relative the outer surface of the body member 131. The angle of the shoulder relative the outer surface can range from approximately 70 degrees to approximately 110 degrees. For example, without limitation, as depicted in FIG. 5A, a shoulder 137 can be formed at each end of the recess, with the angle of each shoulder shown as substantially perpendicular. Furthermore, the recess has a depth d of any suitable dimensions. For example, with reference to FIG. 5A and FIG. 5B, the depth d of the recess 134 can be approximately equal to or greater than a thickness t of the outer tubular member 120. For example, and with reference to a cardiovascular catheter, the thickness t of the outer tubular member 120 is between approximately 0.0025 inches to 0.0035 inches. The depth d can generally range from approximately 0.002 inches to 0.006 inches. Other feasible dimensions for the thickness t and corresponding depth d can be permitted.

Figure 5B:
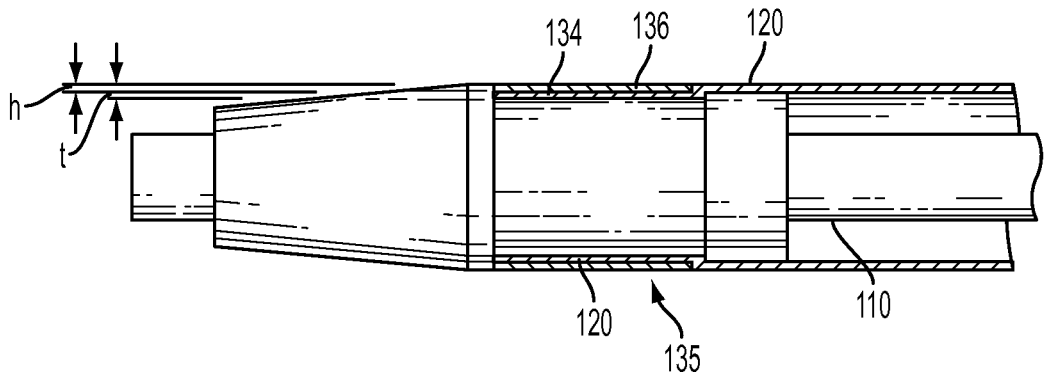
FIG. 5B is a detailed view of a catheter with the movable tubular structure of FIG. 5A in accordance with the disclosed subject matter.
Figure 5C:
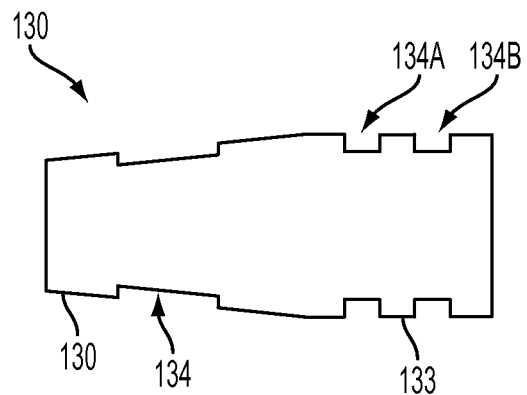
FIG. 5C is a detailed view of another representative embodiment of the movable tubular structure in accordance the disclosed subject matter.

As depicted in FIG. 5B, and in accordance with the disclosed subject matter, the outer tubular member 120 is received within the recess 134 to form a trough 135 along a portion of an exterior surface of the outer tubular member 120. If more than one recess is provided, a second portion of the outer tubular member can be received within the second recess to form a second trough.

As disclosed herein, and in accordance with the disclosed subject matter, the trough 135 has a filler 136 disposed therein to couple the outer tubular member 120 to the body member 131 of the movable tubular structure 130. As embodied herein the filler 136 generally can have a thickness h equal to the depth d of the recess 134. Accordingly, and with reference to the exemplary dimensions above, the thickness h of the filler can range from approximately 0.002 inches to approximately 0.006 inches.

As embodied herein, an exterior surface of the filler 136 is substantially flush with an exterior surface of the outer tubular member 120 adjacent the recess 134. In this manner and as shown in FIG. 5B, a transition between the exterior surface of the filler 136 and the exterior surface of outer tubular member 120 adjacent the recess 134 is substantially smooth. Furthermore, the filler is provided with additional hoop strength to secure the portion of outer tubular member within the recess of the moveable tubular structure. As depicted in FIG. 5B, the filler 136 also abuts the shoulder 137 of the movable tubular structure 130 with the outer tubular member sandwiched therebetween to create the grip and lock. The movable tubular structure 130 and the outer tubular member 120 are thus locked together by the filler 136. Since the outer tubular member 120 is movable with respect to the inner tubular member 110, the movable tubular structure 130 moves with the outer tubular member 120.

The filler can be any suitable material capable of providing sufficient hoop strength to couple the outer tubular member with the recess of the movable tubular member. For example, the filler can comprise at least one of nylon, fluoropolymer, peek, epoxy, platinum iridium, ceramic or metal, such as a metal band or the like. In accordance with a particular aspect of the disclosed subject matter, the filler comprises a material compatible for thermal bonding with a material of the outer tubular member. For example, the material of the filler can comprise the same material as the outer tubular member. The compatibility of the filler and the outer tubular member thus allows for a more secure lock between the outer tubular member and the moveable tubular structure, even if the outer tubular member is not thermally compatible with the movable tubular structure. Additionally, the increased thickness of outer tubular member and filler bonded together with the recess provides a strength that a single layer material does not inherently comprise. Further, a substantially continuous surface of the adjacent outer tubular member with the filler is provided by the heat bond to eliminate an area or edge that could potentially catch while the system is being advanced or withdrawn from the vasculature. Additionally, the mechanical lock created by the filler provides the strength to maintain the integrity of the catheter components. The filler thus can bonded to the outer tubular member by at least one of heat bonding, thermal bonding, adhesive bonding, or the like, as well as by crimping or swaging of a bond of suitable material.

Figure 8:
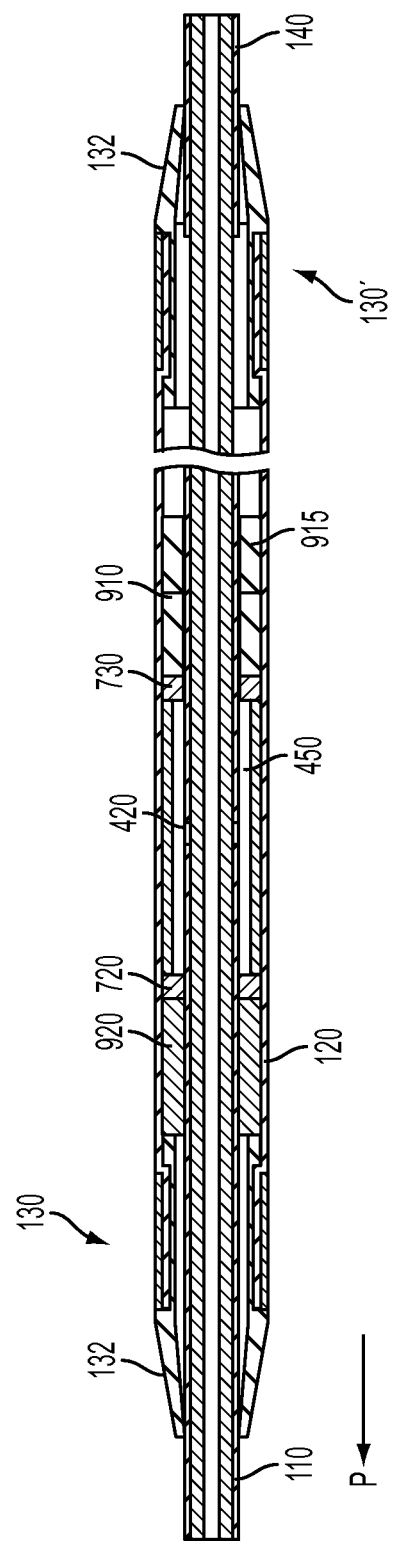
FIG. 8 is a cross sectional view of a catheter having a pressure chamber with proximal and distal movable tubular structures, in accordance with another representative embodiment of the disclosed subject matter.

The movable tubular structure can be disposed along the catheter at any suitable location, depending upon the desired functions and need. The catheter can additionally include more than one movable tubular structure. For example, and as embodied herein, as depicted in FIGS. 4-7, the movable tubular structure 130 can be disposed at the proximal end of the outer tubular member 120. In this embodiment, the movable tubular structure includes a taper segment 132 extending from the proximal end of the outer tubular member 120. The catheter of FIGS. 4, 6, and 7 only includes one movable tubular structure 130. Alternatively, or in addition thereto, the movable tubular structure can be disposed at the distal end of the outer tubular member 120. In the embodiment of FIG. 8, the catheter includes both a proximal movable tubular structure 130 and a distal movable tubular structure 130'. The distal movable tubular structure 130' has a taper segment 132 extending from the distal end of the outer tubular member. However, the proximal movable tubular structure 130 and the distal movable tubular structure 130' can further include other suitable configurations, such as, but not limited to cylinder-type structures with non-tapered segments as recited in the concurrently filed PCT Application Serial No. PCT/US13/68306 entitled "Catheter Having Movable Tubular Structure and Proximal Stopper", the contents of which is incorporated herein by reference in its entirety.

The movable tubular structure can comprise or be made of any suitable biocompatible material, such as PEEK. Because it is not necessary to bond the outer tubular member directly to the movable tubular structure, the movable tubular structure can comprise a material incompatible for thermal bonding with the material of the outer tubular member. As such, it is beneficial for the movable tubular structure to be made of a suitable material having a higher melt temperature than that of the outer tubular member and/or filler Thus, even upon application of thermal energy or heat to the area of the movable tubular structure, the movable tubular structure can maintain its structural integrity. The movable tubular structure can further include a PTFE liner or other low friction or lubricious layer, if desired.

Figure 9:
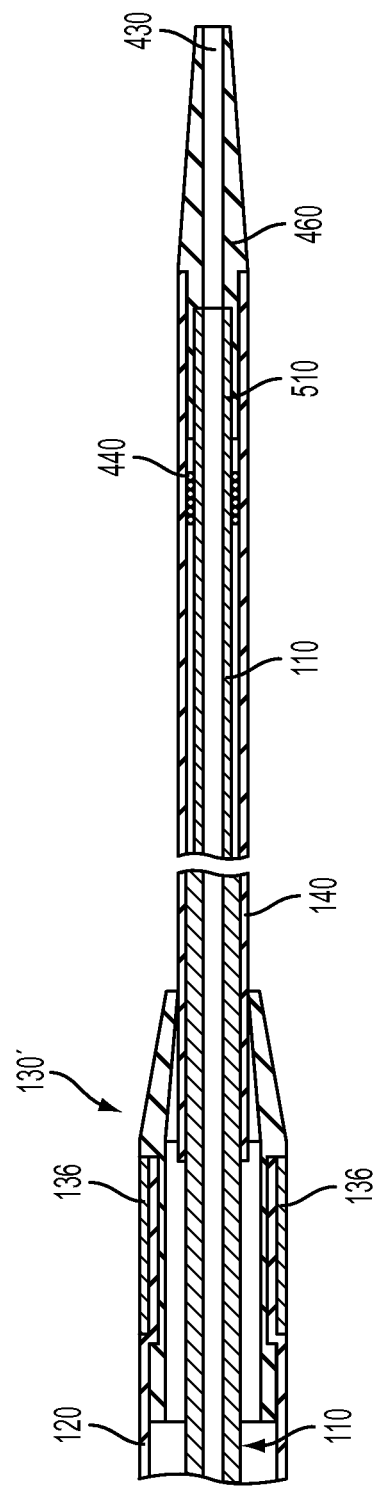
FIG. 9 is a cross sectional view of a catheter having a distal movable tubular structure couple the outer tubular member with a distal sheath, in accordance with yet another representative embodiment of the disclosed subject matter.

In accordance with another aspect of the disclosed subject matter, a distal sheath can be provided, coupled to the outer tubular member by the movable tubular structure. For purpose of illustration, and not limitations, FIG. 9 depicts a catheter having a distal movable tubular structure and distal sheath. As embodied here, the catheter comprises a distal sheath 140 coupled to the outer tubular member 120 by the distal movable tubular member 130'. The distal sheath 140 is thus movable with the outer tubular member 120 and the proximal movable tubular member 130. Accordingly, the distal sheath 140 is movable relative the inner tubular member 110 by movement of the outer tubular member 120. As depicted, the distal sheath 140 can have an outer cross dimension less than an outer cross dimension of the outer tubular member 120. For example, and for use in neuro indications the outer cross dimension of the sheath 140 can be between approximately 4 French to approximately 6 French whereas the distal sheath has an outer cross dimensions of from approximately 0.002 inches to approximately 0.003 inches. The smaller dimension of the sheath 140 allows the sheath to have a flexibility and a stiffness different than a flexibility and stiffness of the outer tubular member 120.

In certain embodiments, such as for neuro indications, the catheter at the distal end along the sheath 140 has a greater flexibility and less stiffness than the catheter along the outer tubular member 120. In another embodiment, such as for peripheral indications, such as below-the-knee procedures, the catheter can have less flexibility and greater stiffness at a distal end e.g., to allow the distal tip to ease through calcified lesions. The distal sheath thus can be made of the same material as the outer tubular member, or can be made of a different suitable material depending upon the intended purpose. For example, the distal sheath for neuro indications can comprise a more flexible softer material that a distal sheath for a below-the-knee indication.

A variety of configurations of the movable tubular structure can be provided to couple the outer tubular member with the distal sheath. For purpose of illustration, and not limitation, and with reference to FIG. 5C, the movable tubular structure can comprise a body member having a base segment with a first recess defined therein and a taper segment with a second recess defined therein. In this manner, the outer tubular member can be coupled to the base segment of the movable tubular structure by a filler as described above. Similarly, a portion of the distal sheath can be disposed within the second recess of the tapered segment of the movable tubular structure, and then a filler of suitable material can be disposed in the trough formed by the distal sheath in the second recess to couple the distal sheath to the moveable tubular structure in a similar manner. Although, the distal sheath can be coupled directly as shown in FIGS. 8-9.

As previously noted, and as embodied in FIGS. 4-7 and 9, the catheter can be used for the delivery of medical devices, such as expandable members and/or stents, disposed along the length of the catheter. Particularly, and as previously noted and as shown in FIG. 4, an expandable member 540 can be coupled to the distal end portion of the inner tubular member 110. The expandable member 540, or balloon as depicted herein, has an exterior surface and an interior surface. The interior surface of the expandable member defines an inner chamber 541. In the embodiment of FIG. 4, the inner chamber 541 is in fluid communication with the inflation lumen 312 of the inner tubular member. In other embodiments as previously discussed, the inner chamber 541 can be in fluid communication with the fluid lumen 310. In such embodiments as shown in detail FIG. 4A, the fluid lumen 310 further includes a directional control valve 452 fluidly coupled with the fluid flow port 420. The directional control valve 452 has a first position in which fluid is directed in the fluid lumen through the fluid flow port 420 into the pressure chamber 450. The directional control valve 452 further has a second position to direct fluid through the fluid lumen 310 into the inner chamber 541 of the expandable member 540 to inflate the expandable member 540 to an inflated configuration.

As depicted respectively in FIG. 4 and FIG. 6, the expandable member is transitionable between a deflated configuration and an inflated configuration. The outer tubular member 120, as described further below, thus can be retracted in a proximal direction to define an exposed length of the expandable member 540. For example, and with reference to the embodiment of FIG. 4, the outer tubular member is retracted to initially expose the stent 440, when the expandable member 540 is then inflated to deploy the stent 440. The expandable member 440 can be subsequently used for dilatation of the luminal walls of the patient with or without a therapeutic agent disposed thereon. Alternatively, the expandable member can be provided without a stent and be used simply for dilatation or delivery of therapeutic agent. With the presence of a therapeutic agent on the expandable member and/or the stent, when provided, the therapeutic agent can be protected by the outer tubular member during delivery of the catheter to a lesion site. Thus, the therapeutic agent is not inadvertently removed during delivery.

Regardless of embodiments with or without one or more stents, the expandable member has an overall length with a working length extending at least a portion of the overall length. The expandable member defines a longitudinal axis and can have suitable shapes along at least a portion of the working length thereof when in the inflated configuration. As embodied herein, for illustration and not limitation, at least a portion of the exterior surface of the expandable member along the working length is configured to engage a body lumen of a patient when the expandable member is in the inflated configuration. In accordance with another aspect of the disclosed subject matter, a variety of different shapes can be used for the expandable member, wherein the shape of the expandable member can depend upon the desired application, such as disclosed in PCT Publication No. WO 2012/037510, entitled "Length and Diameter Adjustable Balloon Catheter", International Application Serial No. PCT/US13/30341, entitled "Length and Diameter Adjustable Balloon Catheter for Drug Delivery", and PCT Publication No. WO 2012/037507, entitled "Length and Diameter Adjustable Balloon Catheter", the disclosures of each of which is incorporated herein by reference in its entirety.

Figure 4B:
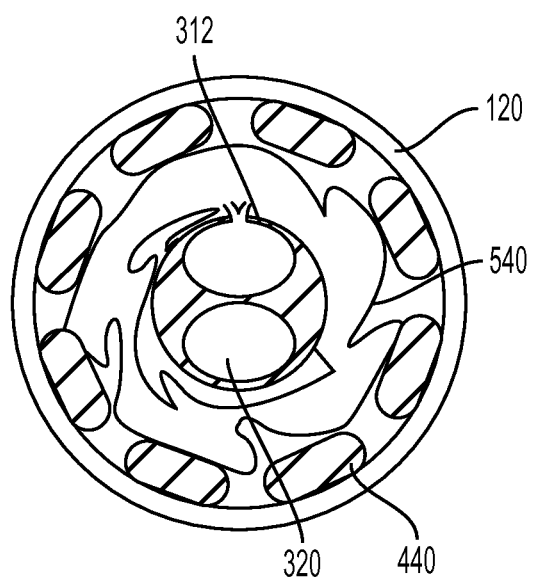
FIG. 4B is a cross sectional view of the catheter of FIG. 4 taken along line 4B-4B.

In accordance with another aspect of the disclosed subject matter, a folded balloon configuration can be used for the expandable member. For example, FIG. 4B depicts an embodiment of a representative cross-section of a distal end of the catheter of FIG. 4 taken along lines 4B-4B. For purpose of illustration, the balloon catheter includes a sheath mounted thereon for delivery. As shown in FIG. 4B, when the outer tubular member 120 is in the extended configuration and positioned over the expandable member 540 and stent 440, the expandable member 540 can be in a folded arrangement within the outer tubular member 120 with the stent 440 crimped thereon. A therapeutic agent can be disposed on the stent and/or expandable member, as desired The outer tubular member is first retracted to expose the desired length of the balloon, e.g. beyond the proximal portion of the stent. The exposed length of the expandable member can then be inflated to deploy the stent, if provided, As such, the working length of the expandable member is no longer folded. A proximal portion of the expandable member can remain within the outer tubular member with the proximal portion folded within the outer tubular member. The folded proximal portion of the expandable member thus facilitates refolding of the expandable member after the expandable member is deflated and the outer tubular member is moved distally.

For purpose of example, the balloon catheter disclosed herein can be used for relatively long balloon lengths, such as peripheral balloons. In certain embodiments, for purpose of example, the expandable member is a long balloon and has a length of approximately 220 mm. The approximate maximum working length of the expandable member can be approximately 200 mm, whereas the approximate folded proximal portion of the expandable member can be approximately 20 mm. Likewise, the refolding technique can be used with an expandable member having a short length, such as approximately 120 mm. In this embodiment, the maximum working length of the expandable member can be approximately 100 mm and the approximate folded proximal portion remaining in the outer tubular member can be approximately 20 mm. The stent disposed on the expandable member can be any suitable length as disclosed herein, and in particular be of a length less than the expandable member.

Figure 4C:
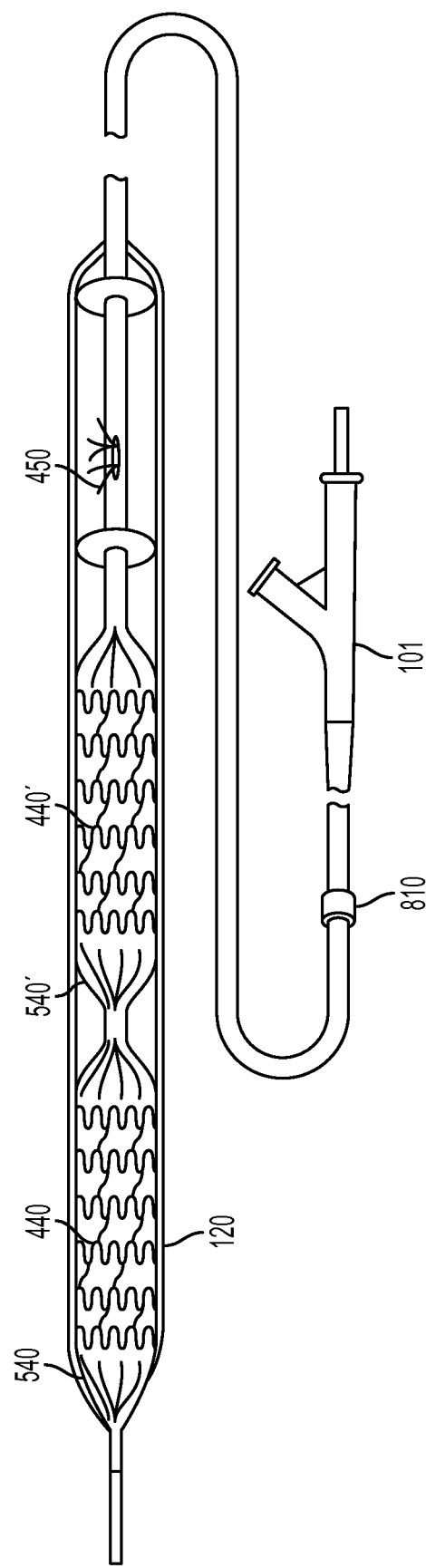
FIG. 4C is a schematic cross sectional perspective side view of a representative catheter have a plurality of expandable members and stents in accordance with the disclosed subject matter.

Other embodiments include the catheter having one or more expandable members and/or stents disposed on the inner tubular member. FIG. 4C shows a representative example of a catheter having a first and second expandable member 540, 540' with a first and second stent 440, 440', according to another embodiment. In such embodiments, the second expandable member 540 is coupled to the distal end portion of the inner tubular member and a second inflation lumen 312' can be provided for the second expandable member 540'. The second expandable member 540' can include a second inner chamber in fluid communication with the second inflation lumen. Similar to the first expandable member 540 as previously discussed, the second expandable member 540' is transitionable between a deflated configuration and an inflated configuration. When a separate second inflation lumen 312 is not provided, the fluid lumen 310 can be used to direct fluid to the second expandable member and the fluid lumen 310 can further include one or more directional control valves.

Although FIG. 4C shows the expandable members 540, 540' having stents 440, 440' disposed thereon, other embodiments contemplate a catheter having the expandable members without the stents disposed thereon or having one of the expandable members with a stent and another of the expandable members without a stent. In any embodiment, the expandable members and/or stents can further includes a therapeutic agent disposed thereon.

Figure 6A:
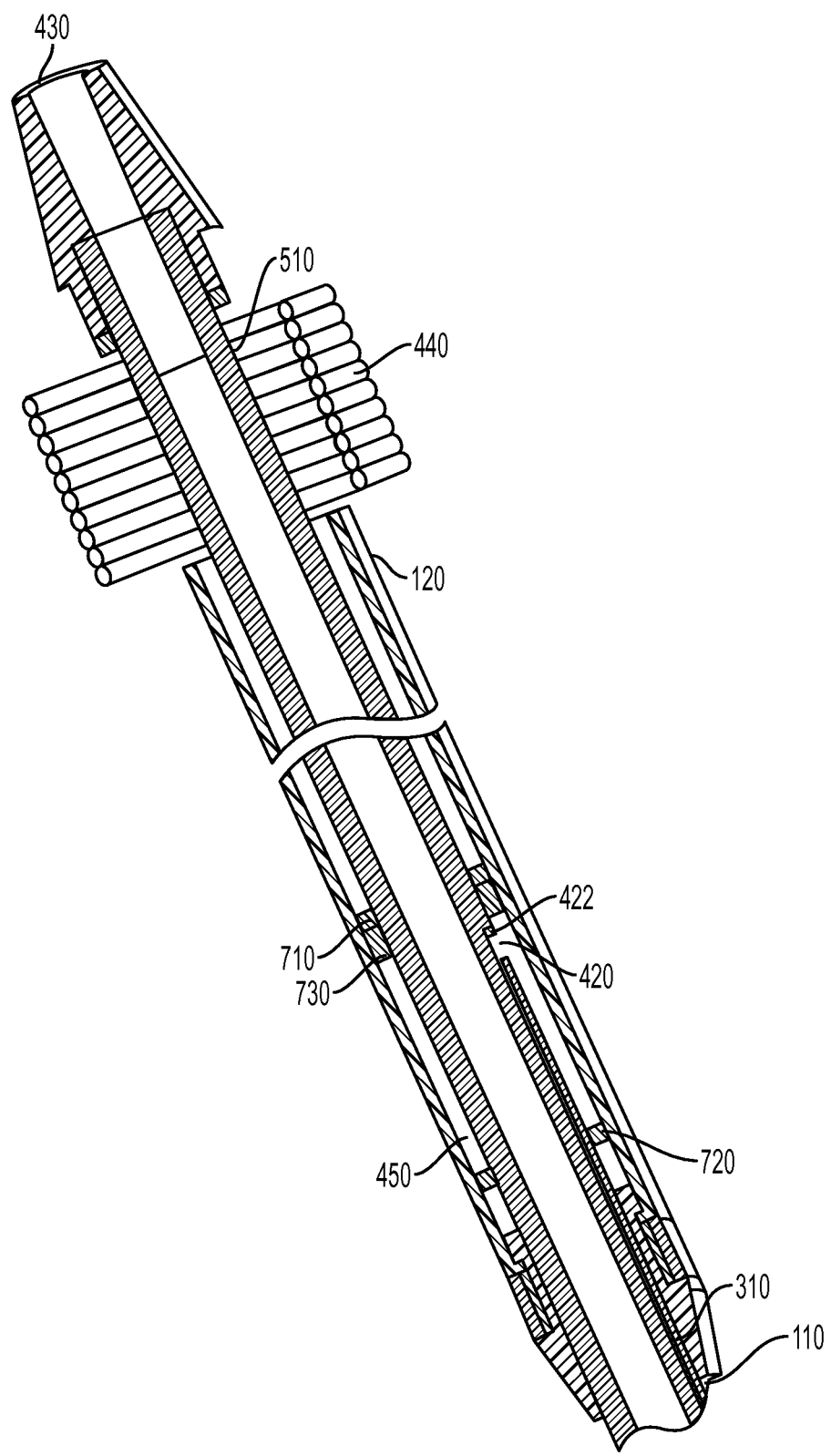
FIG. 6A is a cross sectional side view of the distal end of the catheter of FIG. 4 having a self-expanding stent with the sheath in a fully retracted position.

Other embodiments include the catheter having a self-expanding stent and an expandable member is not required, although can be provided if desired. For example, an expandable member previously described can be provided spaced for the self-expanding stent for sequential deployment. As shown in FIG. 6A, the catheter can include a stent seat 510 for the initial placement of the stent 440, when an expandable member is not present. The stent seat 510 can be disposed proximate the distal end portion of the inner tubular member. However, depending on the intended use and indication, the stent 440 and stent seat 510 can be located at other suitable locations along the catheter for the desired indication. For example, for cardiovascular indications, such as within the heart, the stent and the stent seat can be disposed at the distal end of the outer tubular member. That is, as embodied in FIG. 6A, the stent seat 510 and the stent 440 are disposed at the distal end of the catheter with the outer tubular member 120 retaining the stent 440 at the stent seat. For neuro indications, such as procedures in the brain, the stent seat and the stent can be disposed distal to the outer tubular member at the distal end of the catheter. As embodied in FIG. 9, the distal movable tubular structure 130' couples a distal sheath 140 of smaller cross section with the outer tubular member 120. In this embodiment, the distal sheath 140 retains the stent 440 at the stent seat 410 and the catheter has a smaller cross dimension at the distal end for neuro application. Although reference is made to a stent and stent seat, for purpose of illustration it is recognized that other medical devices also can be delivered by and deployed from the catheter of the disclosed subject matter.

As previously discussed, the outer tubular member 120, and the movable tubular structure 130, as well as the distal the sheath 140, if provided, are movable with respect to the inner tubular member 110, such as to expose a medical device, such as a expandable member or stent. To initiate movement of the components of the catheter, a suitable actuator is provided. For example, and in accordance with another aspect, the catheter can further include a hydraulic pressure chamber at a suitable location along the catheter. Examples of suitable hydraulic pressure chambers include U.S. application Ser. No. 13/467,660, entitled "Catheter Having Hydraulic Actuator" assigned to Abbott Cardiovascular Systems Inc.; U.S. application Ser. No. 13/467,715, entitled "Catheter Hydraulic Actuator with Tandem Chambers" assigned to Abbott Cardiovascular Systems Inc.; and U.S. application Ser. No. 13/467,679, entitled "Catheter Having Dual Balloon Hydraulic Actuator" assigned to Abbott Cardiovascular Systems Inc., the contents of each of which is incorporated herein by reference in its entirety.

Figure 10:
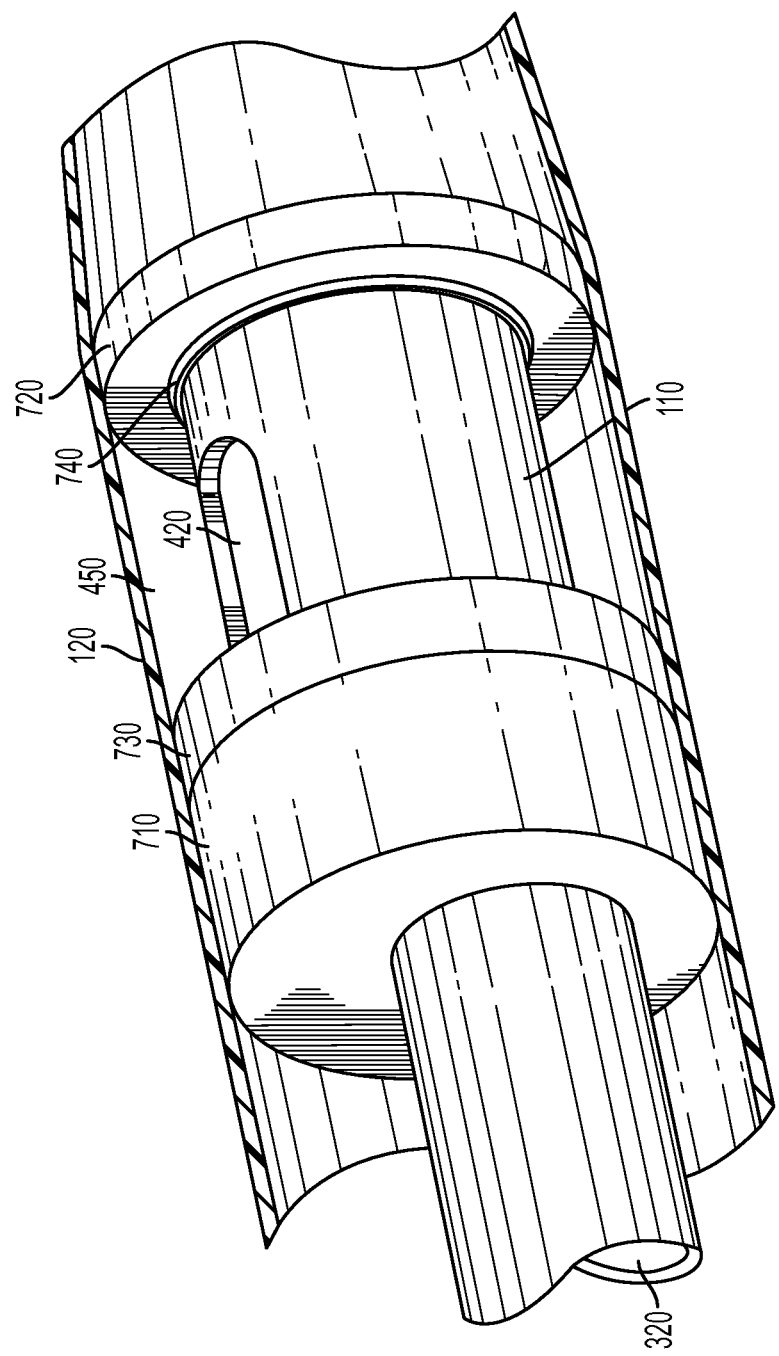
FIG. 10 is a detail perspective view of the catheter of FIG. 4 taken along line FIG. 10.

Solely for purpose of illustration, FIGS. 10 and 11 depict the pressure chamber 450, which is defined between proximal seal 720 and distal seal 730. For purposes of discussion and illustration, other features of the catheter and the pressure chamber are not illustrated herein, but can be understood from the more detailed descriptions incorporated by reference herein. The proximal seal 720 extends from the interior surface of the outer tubular member 120 toward the exterior surface of the inner tubular member 110 and is located proximal to fluid flow port 420. The proximal seal 720 is fixed to the interior surface of the outer tubular member 120 and moves freely relative to the inner tubular member 110. With reference to the embodiment of FIG. 4, the proximal seal 720 is disposed distal to the movable tubular structure 130.

FIGS. 10 and 11 further depict distal seal 730 spaced from the proximal seal 720. The distal seal 730 extends from the exterior surface of the inner tubular member 110 toward the interior surface of the outer tubular member 120 and is located distal to fluid flow port 420. The distal seal 730 is fixed to the exterior surface of the inner tubular member 110 and moves freely relative to the interior surface of the outer tubular member 120. In this manner, the outer tubular member 120 moves freely relative to the distal seal 730. As embodied herein, and as shown in FIG. 9, one or both of the proximal and distal seal can form a wiper seal 740 across the corresponding surface. As such, and as depicted in FIGS. 10 and 11, the pressure chamber is defined by the proximal seal 720, distal seal 730, the exterior surface 111 of the inner tubular member 110, and the interior surface 121 of the outer tubular member 120. Pressure chamber 450 is in fluid communication with fluid flow port 420.

As recognized in the art, the outer tubular member 120 constrains the medical device to be delivered. The medical device, e.g., a self-expanding stent, a stent disposed on an expandable member, or one or more expandable members with or without stents, is deployed by retracting the outer tubular member 120 (catheter sheath). In other embodiments, as previously discussed with respect to FIGS. 8-9, the outer tubular member 120 is connected to sheath 140 via a movable tubular structure 130. The distal sheath 140 retains the stent and the stent is deployed by retracting the outer tubular member 120 along with the distal sheath 140. Retraction is achieved by the introduction of fluid under pressure through the fluid lumen 310 using a conventional device, such as an indeflator or a syringe. The indeflator can include a threaded engagement or other locking mechanism to control pressurization and depressurization of the pressure chamber (not shown). Additionally, a pressure gauge can be provided with the indeflator to monitor the pressure system of the catheter. The indeflator can be configured to allow for the rapid release of hydraulic pressure to stop or inhibit the deployment of the stent. The indeflator can also be configured to create and/or maintain negative pressure in the catheter. The indeflator can further create a vacuum that decreases the profile of the catheter. For example, by creating a vacuum, the outer tubular member 120 disclosed herein, can be configured to decrease in profile and/or lock in position. An example of a suitable indeflator is an Atrion indeflator Atrion Medical—55 ATM.

With reference to FIG. 4C, an adapter or manifold 101 can be provided at the proximal end of the catheter for access to the fluid lumen and inflation lumen, when provided, and can be configured for connecting to a fluid source (not shown). For example, the manifold can have a Y-shape with a luer connector at the proximal end of one branch to receive the fluid source, and a separate hemostatic valve on another branch to receive a guidewire. A conventional device, such as but not limited to an indeflator or a syringe as previously discussed, can be connected to the luer connector to introduce the fluid to the fluid lumen. A locking mechanism can further be provided to lock the operating position of the indeflator or syringe. The manifold can include additional branches to accommodate the inflation lumen, if needed.

With reference to FIG. 10, fluid is introduced into the fluid lumen and exits the fluid lumen at flow port 420 and fills pressure chamber 450. Once sufficient fluid is introduced into the pressure chamber 450, a force is applied on the distal and proximal seals. Because the distal seal 730 is fixed relative to the inner member, only the proximal seal 720 and outer tubular member 120 attached thereto is capable of movement relative to the inner member in the proximal direction P. Movement of the proximal seal 720 upon the application of force in the pressure chamber 450 urges the outer tubular member 120, along with the movable tubular structure 130 and distal sheath 140 if provided, to move in the proximal direction P along the inner tubular member thereby allowing the medical device to be deployed. Distal seal 730, as embodied herein, is configured as a wiper-seal with the interior surface of outer tubular member 120. The outer tubular member 120, and the movable tubular structure 130 and sheath 140 if provided, thus move relative to distal seal 730. Proximal seal 720 mounted to the interior surface of outer tubular member 120 is configured as a wiper-seal with the exterior surface 111 of inner tubular member 110. The proximal seal 720 is free to move relative to the inner tubular member 110.

Furthermore, by providing a movable tubular structure 130 and distal sheath 140, the pressure chamber 450 can be sufficiently spaced proximal to the distal end of the catheter and the stent seat for neuro indications or the like. Thus, the pressure chamber 450 can be disposed at the proximal portion of the catheter. For instance, the pressure chamber 450 can be spaced approximately 8 inches to approximately 20 inches from the stent 410 and stent seat 510. This spaced relationship between the pressure chamber to the stent provides certain safety benefits if a mechanical issue arises within the pressure chamber; e.g., maintains spaced relations from the brain. However, in other embodiments, the pressure chamber can be disposed at any location along the catheter as discussed in the concurrently filed International Application No. PCT/US13/68306 entitled "Catheter Having Movable Tubular Structure and Proximal Stopper", the contents of which are incorporated herein by reference in its entirety.

Regardless of the positioning of the pressure chamber along the catheter, the catheter can additionally include a proximal stopper disposed proximal to the pressure chamber to limit the movement of the outer tubular member and the movable tubular structure in the proximal direction. FIG. 4 depicts a proximal stopper 801 disposed proximal to a proximal end of the proximal movable tubular structure 130. Accordingly as shown in FIG. 4C, the proximal stopper 801 can be disposed distal to the proximal adapter at any suitable location along the catheter to allow engagement of the distal end of the outer tubular member 120 with the proximal stopper 801. As such, the proximal stopper inhibits movement of the outer tubular member in the proximal direction. The proximal stopper can be any suitable dimension or size suitable to inhibit movement of the outer tubular member distal thereof. The proximal stopper can comprise any suitable material, such as, but not limited to the materials suitable for the movable tubular structures. The proximal stopper can additionally include materials such as for purposes of example, but not limited to, stainless steel, ceramics, polyetheretherketone (PEEK), polyphenylene sulfide (PPS), polyether imide (PEI), and polysulfone (PS).

Although shown as a single piece seal construction in FIGS. 10 and 11, each seal of the disclosed subject matter can be a multi-piece seal assembly, if desired. For example, the seal assembly can include a seal member and a bushing to provide a backing to the seal member, as known in the art. As depicted in FIG. 8, the seals 720 and 730 can further be supported by a spacer device, such as proximal and distal bushings 920 and 910, respectively. In the embodiment of FIG. 8, the proximal bushing 920 is disposed external to the pressure chamber, such as between the proximal seal 720 the proximal movable tubular structure 130 and the distal bushing 910 is disposed external to the pressure chamber, such as between the distal seal 730 and the distal movable tubular structure 130. Additional spacer devices can be provided as desired. The catheter can further include a stopper member 915 coupled to the inner tubular member 110 distal to the distal seal 730 for additional support. In FIG. 8, a bushing 910 is disposed between the distal seal 730 and the stopper member 915. The stopper and bushings can be constructed of any suitable material, including, but not limited to, PEEK, Pebax, HDPE, LDPE, a mixture of HDPE and LDPE, a Nylon blend such as L75/L25, or the like. Furthermore, the bushings can comprise a metallic material, combination low density polyethelene, silicon, nitril, soft Pebax 30, or other blends of suitable material, and can be coated with a suitable material as known in the art, and can include a coating.

As relatively high fluid pressures are needed to retract outer tubular member 120, the pressure chamber is formed to withstand such pressures with minimal to no leaks. A variety of suitable seal constructions and materials can be used, such as, but not limited to, sliding seals, rings, cups seals, lips seals, and compressed bushings. For example, each seal can be formed as a separate member and attached to the corresponding tube member, or can be formed as part of the tubular member. Solely for purposes of illustration, a hydrophilic material, such as, but not limited to, HydroMed™, Hydrothane™, Hydak®, can be used for the seals. Seals made of such material can be configured to swell when exposed to an aqueous environment, thus sealing more tightly while maintaining lubricity. The seals thus can comprise an expandable material or composite of materials to increase accordingly to match the dimensions of the outer tubular member. That is, the seal can be configured to expand with the outer tubular member to maintain an adequate seal.

As the pressure chamber expands, the exposed surface area of the seal can also increase, resulting in a proportional increase in retraction force at a given fluid pressure. Thus, an expanding pressure chamber provides for greater retraction force at a given pressure. Seals made of such material can be configured to swell when exposed to an aqueous environment, thus sealing more tightly while maintaining lubricity. Alternatively, the proximal and distal seals can be coated with a hydrophobic layer such as oil or wax or made of hydrophobic material such as a fluorocarbon or olefins like polypropylene to be used with a suitable pressurized fluid, to prevent swelling of the seals. Solely for example, silicone seals can be provided with a Hydromer 2314-172 coating. In another embodiment, O-rings can be used for the seal constructions comprised of silicone, bona, or other suitable elastomers. Furthermore, solely for purpose of example, the seal can include soft tubing such as a low durometer Pebax. Additionally or alternatively, a high viscosity hydraulic fluid can be used to inhibit leaks.

Embodiments of the disclosed subject matter allow the pressure chamber to operate with a variety of different suitable pressures. Solely for purpose of example, in certain embodiments the pressure chamber can handle a positive pressure of up to 750 psi, and a negative pressure of approximately 14 psi. An exemplary operating parameter for a cardiovascular catheter indications can operate at pressures ranging up to approximately 40 to 50 ATM (or about 588-735 psi).

In accordance with another aspect, the catheter further can include bellows, or a bladder component (not shown) within the chamber to prevent leaks. The bellows or bladder component is attached to the exterior surface of the inner tubular member and is in fluid communication with the fluid flow port, wherein fluid introduced through the fluid flow port expands the bellows component to further retract the outer tubular member.

In yet another aspect of the disclosed subject matter, spacer elements (not shown) can be provided within the pressure chamber. The spacer elements can prevent the outer tubular member, proximal seal and distal seal from being collapsed during delivery and storage of the catheter. The spacer elements can also reduce the amount of fluid needed to retract the outer tubular member. The spacer elements can be made of any of a variety of suitable shapes and materials, such as ring members having diameters corresponding to the inner and outer diameters of the inner and outer tubular members, respectively.

If desired, the distal seal can form a bumper or stop member for the medical device, such as a stent. In other embodiments, the pressure chamber 450 is spaced from the medical device to be delivered, such as by the use of a distal sheath as previously discussed herein. Alternatively, in accordance with another aspect of the disclosed subject matter, the catheter can include a stop 710 secured to the inner tubular member 110, as depicted in FIGS. 10 and 11. The stop is disposed distal to the pressure chamber 450 and proximal to the medical device to be delivered, e.g., the stent. In this manner, the stop 710 seals the hydraulic fluid lumen 310 but allows the guidewire tube 321 and/or guidewire (not shown) to pass through. Stop 710 can be made of or include a radiopaque material to provide the physician performing the procedure with visibility as to placement of the catheter so that the medical device can accurately be positioned at the treatment site. The stop 710 is thus a radiopaque marker. For example, the marker can be a radiopaque metallic ring, or made of a tungsten loaded polymer for increased softness and flexibility. Other suitable markers known can be used.

In accordance with another aspect of the disclosed subject matter, other devices, such as a spring, can be provided to bias the outer tubular member 120 in the proximal direction P. Examples of springs and other devices that can be implemented with embodiments of the subject matter can be found in U.S. application Ser. No. 13/467,660, entitled "Catheter having Hydraulic Actuator" by Michael Bialas and Michael Green and owned by Abbott Cardiovascular Systems Inc.; U.S. application Ser. No. 13/467,679, entitled "Catheter having Dual Balloon Hydraulic Actuator" by Michael Green and Michael Bialas and owned by Abbott Cardiovascular Systems Inc.; and U.S. application Ser. No. 13/467,715, entitled "Catheter having Hydraulic Actuator with Tandem Chambers" by Michael Green and Michael Bialas, the contents of which are herein incorporated by reference in their entirety.

Reference is now made to FIG. 7, solely for purposes of illustration, which depicts an over-the-wire variation of the disclosed subject matter. In this embodiment, catheter 100 includes inner tubular member 110, outer tubular member 120 (shown in a retracted position), a guidewire lumen 320, and fluid lumen 310 having fluid flow port 420. Catheter 100 further includes medical devices, such as stent 440 as shown in an expanded state, stent seat 510, and a distal guidewire port 430.

As shown in FIG. 7A, solely for the purpose of illustration, the inner tubular member 110 or elongated catheter shaft of the catheter can include first and second tubular members 110 and 610, respectively, in coaxial relationship with each other to define a central guidewire lumen 320 within the first tubular member 110 and an annular fluid lumen 310 located between the first and second tubular members 610 of the inner tubular member or shaft. The fluid lumen 310 can supply a hydraulic medium under positive pressure and can withdraw the hydraulic medium, i.e., provide negative pressure, from pressure chamber 450 as desired. The catheter is sized and configured for delivery within a corresponding body lumen for the intended indication, such as a vasculature for vascular intervention. The catheter includes a guidewire lumen for delivery over a guidewire 620 as shown in FIG. 7A. For example, in certain embodiments such as for neuro indications, the catheter can be 0.012 or 0.010 guidewire compatible. The portion of the inner tubular member extending distal of the chamber can be defined by an extension of the first tubular member 110, or an extension of the second tubular member 610, or by a separate tubular member as desired. Although a coaxial shaft and over-the-wire (OTW) catheter configuration is depicted in FIG. 7, those skilled in the art will recognize that other configurations and known materials of construction can be used without departing from the scope of the disclosed subject matter, for example, the rapid exchange and/or dual lumen configurations as previously described.

The pressure chamber 450 can additionally include a locking system to prevent the outer tubular member 120 from prematurely moving in the proximal direction P. The pressure chamber 450 with the locking system operates substantially the same as previously described. However, the locking system restricts the initial movement of the outer tubular member until suitable pressure is first introduced into the chamber. Examples of suitable locking systems can be found in the currently pending U.S. application Ser. No. 13/797,636, entitled, "Catheter Having Hydraulic Actuator And Locking System", assigned to Abbott Cardiovascular Systems Inc. and filed on Mar. 12, 2013, the contents of which are incorporated by reference herein in its entirety.

In accordance with another aspect of the disclosed subject matter, a method of making a catheter is furthermore disclosed. The method includes, among other things, providing an inner tubular member having a proximal end portion, a distal end portion and an exterior surface. The inner tubular member further has a guidewire lumen defined therein. An outer tubular member movable relative to the inner tubular member is provided. The outer tubular member has a proximal end, a distal end and an interior surface directed toward the exterior surface of the inner tubular member.

Details regarding the material of the disclosed subject are understood from the detailed description above. Generally, however, a movable tubular structure is located between the outer tubular member and the inner tubular member. The movable tubular structure includes a body member having an outer surface with a recess defined therein. The outer tubular member is received within the recess to form a trough along a portion of an exterior surface of the outer tubular member. A filler is disposed in the trough. The filler has a suitable hoop strength to couple the outer tubular member to the body member of the movable tubular structure. As indicated above, the filler can be any of a variety of suitable materials. For example, if a thermally compatible material is provided to bond with the outer tubular member, then the method can further include providing a shrink wrap over the filler at the trough. The filler is thermally bonded with the outer tubular member to secure the outer tubular member with the movable tubular structure and the shrink wrap is removed. A similar method can be used to couple the distal sheath if provided, to the movable tubular structure. Other bonding techniques are further contemplated herein, as previously discussed.

In accordance with the embodiments of the subject matter previously described, the components of the catheter can be made of a variety of suitable materials. For example, the proximal and distal seals of the expandable chamber configuration can be formed of any suitable materials. Solely for example, the seals can be rubber or silicon. In embodiments having an expandable pressure chamber, the seals can be formed of a low durometer rubber having a compressed condition and an expanded condition. The seals can be significantly compressed and deformed in the initial delivery configuration, transitioning to the expanded condition when the pressure chamber is pressurized. Alternatively, the seals can be made of hydrophilic polymers that absorb fluid in the pressure chamber and expand along with the outer tubular member. Alternatively, the proximal and distal seals can be made of hydrophobic material.

The inner tubular member and outer tubular member each can be a single piece construction, or an assembly of components, and can be made of any suitable material. For example, suitable materials include, but are not limited to polymer materials such as nylon, urethane, polyurethane, PEEK, PTFE, PVDF, fluoropolymer such as Kynar, PE, HDPE, a trilayer material including L25, Plexar, PEBAX, or polyethylene of various suitable densities. For example, the outer tubular member can comprise a nylon braided tube with a PTFE liner. Additionally a lubricious liner, such as PTFE, on the inside diameter of the outer tubular member, or the sheath, allows the stent to deploy with low force and can prevent the outer tubular member from being bonded to the stent or other catheter components. In another example, the outer tubular member includes a fluoropolymer braided tube with lubricous liner. Furthermore, at least a portion of the inner and/or outer tubular members can be constructed of an alloy or metallic material, such as stainless steel hypodermic tubing or the like.

As a further alternative, the inner tubular member and/or the outer member each can be constructed of multiple outer tubular members. A stop can further form a joint for two adjacent tubular members. The outer tubular member can further be constructed of a composite comprising a fabrication of several different materials, such as a co-extrusion of different polymers, or a fiber-reinforced composite material such as fiber reinforced resin materials or braided materials. Solely for example, exemplary embodiments can include a braided tube with a PTFE liner, a Polymide middle layer with braiding and a Pebax 72D outer layer. Additionally, to improve flexibility, helical or spiral member configurations can be used in the construction of the inner and outer tubular members.

Exemplary constructions for the outer tubular member include a single layer of polyimide or PEEK; a trilayer material of L25, Plexar, HDPE; or a braided tube with a PTFE liner, a Polyimide middle layer braiding middle layer, and a Pebax 72D outer layer. The inner and/or outer tubular members can also be reinforced by the addition of a strengthening member, such as, for example, a wire coil. In certain embodiments, the inner tubular member is reinforced by the addition of a strengthening member along a length corresponding to the pressure chamber.

It is further contemplated that the inner and outer tubular members can be constructed of other biocompatible material. As such, the inner and outer tubular members of the catheter can be constructed from the above-identified polymers, combinations or blends of these polymers, whether alone or in combination with other materials, or other bioabsorbable materials.

The inner and outer tubular members can be manufactured using a variety of known techniques such as but not limited to: extrusion, injection molding, air-blowing, stretching, deep drawing, polymerization, cross-linking, dipping from solution, powder depositioning, sintering, electrospinning, melt spinning, deformation under temperature, stretch blowing, chemical grafting any combination of the above with reinforcement element like metal braids, coils, glass fibers, carbon fibers and other kind of organic or inorganic fibers, liquid crystals, as well as classical machining technologies like milling, drilling, grinding, etc. In the event that metallic elements such as hypotubes are to be incorporated, various metallic manufacturing techniques can be used, such as but not limited to, machining, tube drawing processes, drilling, milling, EDM, other deformation methods, plating, sputtering, electrografting, sintering, and depositioning e-polishing, among others. In certain embodiments of the disclosed subject matter, the inner tubular member includes a stainless steel hypotube at least at its proximal end.

Additionally, the inner and outer tubular members can be constructed from PE, polypropylene, Kynar, or urethane by an extrusion process using an extruder such as that available from any of a number of known suppliers. The materials can be post-processed in a number of ways including, for example and not by way of limitation, extrusion, molding, such as by injection or dipping, textile processing such as weaving or braiding, and forming. Forming processes that can be suitable are rolling and welding sheets of material or vacuum forming into tubular shapes, to name only a few examples.

The inner and outer tubular members can be further coated with any of a variety of materials and techniques to enhance performance if desired, including a number of suitable coatings and coating techniques subject to patent matters owned by Abbott Laboratories such as U.S. Pat. Nos. 6,541,116, 6,287,285, and 6,541,116, the entireties of which are hereby incorporated by reference. For example, possible coating materials include lubricious materials such as Teflon®, and hydrophobic materials such as silicone lubricant dispersion PN 4097, or hydrophilic materials such as hydrogel, or lubricious coatings.

The inner and outer tubular members can have any suitable cross-sectional shape, including elliptical, polygon, or prismatic, although a circular cross-section generally is preferred. The inner and outer tubular members can also have any suitable size and diameter depending upon the desired application. The catheter is suitably sized and configured for delivery within a corresponding body lumen for the intended indication, such as a vasculature for vascular intervention.

According to certain embodiments, the outer tubular member can include an outer layer and an inner layer. The outer tubular member can be provided with an inner layer attached to or formed with an outer layer. The inner layer or liner can include a lubricious material to facilitate the sliding of the outer tubular member in a proximal direction when the outer tubular member is retracted. For example, different types of polymers such as PTFE or high-density polyethylene (HDPE) can be used for the inner layer. Additionally, other lubricious polymers can be used. The outer layer, as embodied herein, provides sufficient strength to capture a medical device therein, as well as allow movement between the first position and the second position. The multiple layers can be formed separately and adhered or bonded together or co-extruded as a single member.

In further accordance with the disclosed subject matter the outer tubular member can include a reinforcing layer disposed between the outer layer and the inner layer, such as a braided material. For example, the reinforcing layer can be provided in the form of a braided stainless steel tube or sheet or the like. The braid can include flattened filaments, as opposed to having filaments with a round cross-section. Alternatively, the reinforcement can be in the form of a tube including woven fabric or appropriately oriented filaments, such as carbon fibers encased in a polymeric matrix. Likewise, such reinforcing fibers could additionally or alternatively be incorporated into inner layer and/or outer layer during the manufacturing process.

When the outer tubular member is provided with an inner layer, outer layer and a reinforcing layer, the outer tubular member can be formed in the following manner. First, inner layer is formed through a tubular extrusion process, and disposed about a forming mandrel (not shown). The forming mandrel, as embodied herein, has a shape that corresponds to the desired shape of the inside of the outer tubular member. Next, the reinforcing layer, which can be provided in the form of a stainless steel braid material, is positioned over a predetermined length of inner layer. Next, the outer layer is extruded and positioned over the reinforcing layer. The outer layer can be provided in the form of two separate tubular members that are overlapped slightly at their ends over reinforcing layer. Each portion of outer layer can be a different material selected to provide a different durometer as described above. The two portions of outer layer can overlap by an amount such as approximately 0.1 inches. Next, a sleeve of heat shrinkable material is positioned over the entire outer tubular member assembly. Finally, heat is applied to the assembly. When heat is applied, the heat shrinkable tubing shrinks, and causes inner layer to fuse with outer layer, trapping reinforcing layer therebetween. The heating process also causes inner layer to conform to the shape of the forming mandrel. After the assembly cools, the heat shrinkable tubing is cut away, leaving behind the outer tubular member.

As previously noted, if an expandable member is provided, a wide variety of suitable materials can be used for the expandable member or balloon in accordance with the disclosed subject matter. For example, the expandable member can be made from polymeric material, including compliant, semi-compliant, or non-compliant polymeric material or polymeric blends.

In certain embodiments, the polymeric material is a polyamide/polyether block copolymer (commonly referred to as PEBA or polyether-block-amide). The polyamide and polyether segments of the block copolymers can be linked through amide or ester linkages. The polyamide block can be selected from various aliphatic or aromatic polyamides known in the art. Some non-limiting examples of an aliphatic include nylon 12, nylon 11, nylon 9, nylon 6, nylon 6/12, nylon 6/11, nylon 6/9, and nylon 6/6. In certain embodiments, the polyamide is nylon 12. The polyether block can be selected from various polyethers known in the art. Some non-limiting examples of polyether segments include poly(tetramethylene ether), tetramethylene ether, polyethylene glycol, polypropylene glycol, poly(pentamethylene ether) and poly(hexamethylene ether). Commercially available PEBA material can also be utilized such as for example, PEBAX® materials supplied by Arkema (France). Additionally balloon grillamid can be used as the material for the expandable member. Various techniques for forming a balloon from polyamide/polyether block copolymer are known in the art. One such example is disclosed in U.S. Pat. No. 6,406,457 to Wang, the disclosure of which is incorporated by reference in its entirety.

In another embodiment, the expandable member is formed from polyamides. The polyamide can have substantial tensile strength, is resistant to pin-holing even after folding and unfolding, and is generally scratch resistant, such as those disclosed in U.S. Pat. No. 6,500,148 to Pinchuk, the disclosure of which is incorporated herein by reference in its entirety. Some non-limiting examples of polyamide materials suitable for the balloon include nylon 12, nylon 11, nylon 9, nylon 69 and nylon 66. Other suitable materials for constructing non-compliant balloons are polyesters such as polyethylene terephthalate) (PET), Hytrel thermoplastic polyester, and poly(ethylene.

In another embodiment, the balloon is formed of a polyurethane material, such as TECOTHANE® (Thermedics). TECOTHANE® is a thermoplastic, aromatic, polyether polyurethane synthesized from methylene disocyanate (MDI), polytetramethylene ether glycol (PTMEG) and 1,4 butanediol chain extender. TECOTHANE® grade 1065D can be used and has a Shore durometer of 65D, an elongation at break of about 300%, and a high tensile strength at yield of about 10,000 psi. However, other suitable grades can be used, including TECOTHANE® 1075D, having a Shore D hardness of 75. Other suitable compliant polymeric materials include ENGAGE® (DuPont Dow Elastomers (an ethylene alpha-olefin polymer)) and EXACT® (Exxon Chemical), both of which are thermoplastic polymers. Other suitable compliant materials include, but are not limited to, elastomeric silicones, latexes, and urethanes.

The compliant material can be cross linked or uncrosslinked, depending upon the balloon material and characteristics required for a particular application. The polyurethane balloon materials are not crosslinked. However, other suitable materials, such as the polyolefinic polymers ENGAGE® and EXACT®, can be crosslinked. By cross-linking the balloon compliant material, the final inflated balloon size can be controlled. Conventional crosslinking techniques can be used including thermal treatment and E-beam exposure. After crosslinking, initial pressurization, expansion, and preshrinking, the balloon will thereafter expand in a controlled manner to a reproducible diameter in response to a given inflation pressure, and thereby avoid over expanding the balloon to an undesirably large diameter.

In another embodiment, the balloon is formed from a low tensile set polymer such as a silicone-polyurethane copolymer. The silicone-polyurethane can be an ether urethane and more specifically an aliphatic ether urethane such as PURSIL AL 575A and PURSIL ALIO, (Polymer Technology Group), and ELAST-EON 3-70A (Elastomedics), which are silicone polyether urethane copolymers, and more specifically, aliphatic ether urethane cosiloxanes. In an alternative embodiment, the low tensile set polymer is a diene polymer. A variety of suitable diene polymers can be used such as, but not limited to, an isoprene such as an AB and ABA poly (styrene-block-isoprene), a neoprene, an AB and ABA poly (styrene-block-butadiene) such as styrene butadiene styrene (SBS) and styrene butadiene rubber (SBR), and 1,4-polybutadiene. In certain embodiments, the diene polymer is an isoprene including isoprene copolymers and isoprene block copolymers such as poly(styrene-block-isoprene).

In certain embodiments, the isoprene is a styrene-isoprene-styrene block copolymer, such as Kraton 1161K available from Kraton, Inc. However, a variety of suitable isoprenes can be used including HT 200 available from Apex Medical, Kraton R 310 available from Kraton, and isoprene (i.e., 2-methyl-1,3-butadiene) available from Dupont Elastomers. Neoprene grades useful in the disclosed subject matter include HT 501 available from Apex Medical, and neoprene (i.e., polychloroprene) available from Dupont Elastomers, including Neoprene G, W, T and A types available from Dupont Elastomers. Examples of other balloon and catheter embodiments which can be employed in accordance with the disclosed subject matter include U.S. Pat. Nos. 4,748,982; 5,496,346; 5,626,600; 5,300,085; and 6,406,457 and application Ser. Nos. 12/371,426; 11/539,944; and 12/371,422, each of which is hereby incorporated by reference in its entirety.

In accordance with another aspect of the disclosed subject matter, the expandable member is a balloon having a multilayer construction. The multilayer construction can include at least a first layer and a second layer having a combined wall thickness. As embodied herein, for purpose of illustration and not limitation, the first layer is made of a first polymer material having a first maximum blow-up-ratio, and the second layer is made of a second polymer material having a second maximum blow-up-ratio greater than the first maximum blow-up-ratio. The at least first and second layers define a compliance less than that of a single layer made of the first polymer material with a wall thickness equal to the combined wall thickness.

A multilayered balloon of the disclosed subject matter can be formed in whole or in part of coextruded polymeric tubular layers, and provides for ease of manufacture of the balloon and balloon catheter formed therefrom. The multilayered balloon is typically formed by conventional blow-molding in which a multilayered polymeric tube is radially expanded within a balloon mold. The resulting multilayered balloon has an inflated shape which corresponds to the inner surface of the mold and which has a diameter about equal to the inner diameter of the balloon mold, commonly referred to as the balloon's nominal working diameter. The nominal pressure is the inflation pressure required to fill the balloon to the nominal working diameter. In accordance with the disclosed subject matter, the balloon expands a very small amount (i.e., noncompliantly) at pressures above the nominal pressure. As a result, the balloon minimizes injury to a patient's blood vessel, which can otherwise occur if the balloon continues to expand a substantial uncontrolled amount at increasing inflation pressures above nominal.

The blow-up-ratio (BUR) of the balloon formed from a polymer tube should be understood to refer to the ratio of the outer diameter of the blown balloon expanded within the mold (i.e., the mold inner diameter) to the inner diameter of the polymer tube prior to being expanded in the mold. Each individual layer of the multilayered balloon similarly has its own BUR based on the ratio of the inner diameter of the mold and the inner diameter (prior to expansion in the mold) of the layer of the polymeric tube. For a given balloon wall thickness, the rupture strength generally increases and the radial compliance decreases as the balloon BUR increases. For standard pressure driven blow molding of catheter balloons, typical BURs range from about 4.5 to about 8.0 depending on the material and the product application.

A multilayer balloon in accordance with the disclosed subject matter increases the amount of balloon material that is highly oriented in the radial direction, to provide a balloon with limited radial expansion at increasing inflation pressures (i.e., to provide a noncompliant balloon). Specifically, a multilayered balloon of the disclosed subject matter has polymeric materials that can be expanded to higher BURs as the inner layer(s) of the balloon, while lower BUR materials are the outer layer(s) of the balloon. In certain embodiments, the balloon has a first layer of a first polymeric material and a second layer of a second polymeric material which has a lower Shore durometer hardness than the first polymeric material and which can be expanded during balloon blowing to a higher BUR (without rupturing or tearing) than the higher Shore durometer hardness material of the first layer, and the second layer is an inner layer relative to the first layer. For example, in certain embodiments, the multilayered balloon inner layer is formed of a polyether block amide (PEBA) material (e.g., commercially available as PEBAX®) having a Shore durometer hardness of about 60-70D while the outer layer is formed of a PEBA material having a higher Shore durometer hardness of about 70-72D. However, a variety of suitable materials can be used including materials which are of the same material classification/family, or different classes of materials. The multilayered balloon generally has two or more layers (i.e., layers formed of materials which differ in some respect such as different Shore durometer hardnesses), although it typically does not have more than five layers.

Despite presence of the lower durometer material forming the second (inner) layer of the multilayered balloon, a multilayer balloon of the disclosed subject matter provides a balloon which has a very low compliance. For example, a balloon of the disclosed subject matter having a first (outer) layer of a first durometer, and one or more inner layer(s) of successively lower durometers (i.e., increasingly softer materials), has a lower compliance than a balloon having about the same wall thickness but formed of 100% of the highest durometer material (i.e., the material forming the outer-most layer of the balloon of the disclosed subject matter). Compared to a balloon formed of 100% of the highest durometer material, a balloon of the disclosed subject matter has effectively replaced a part of the balloon wall thickness with the layer(s) of lower durometer (softer) material(s), which would typically be expected to increase the compliance. While not wishing to be bound by theory, it is believed that the balloon provides the noncompliant behavior through the specific combination of highly oriented layers of the balloon, and particularly by maximizing the orientation of the inner layer(s) of the balloon. The inner layer orientation significantly affects compliance of the balloon. By selecting and arranging different materials that can be blown to different BURs in accordance with the disclosed subject matter, the balloon has layers with successively increasing BURs from the outer to the inner layer(s), such that the BUR of each layer can be maximized and the inner layer(s) have particularly high BURs. The layers of the balloon are therefore optimized for compliance purposes. Although additional layers may be added to the balloon, to, for example, increase the total wall thickness to a desired value, the arrangement of the basic layers in accordance with the disclosed subject matter cannot be varied without resulting in a higher compliance balloon.

Additionally, the disclosed subject matter can alternatively provide for a multilayer balloon with a low compliance but with very thin walls. For example, certain embodiments are directed to a multilayered balloon having a first (outer) layer of a first durometer material and one or more inner layer(s) of successively lower durometer materials which has a compliance not substantially greater than (e.g., not more than about 10% to about 20% greater than), and approximately about equal to a balloon which is formed of 100% of the highest durometer material but which has a larger wall thickness than the multilayered balloon of the disclosed subject matter. The embodiment of the balloon having a very thin total wall thickness provides an improved low profile and flexibility due to the thinner walls of the balloon, but, in accordance with the disclosed subject matter, nonetheless continues to provide a low compliance despite the thin wall.

The rupture pressure and compliance of a balloon are affected by the strength (e.g., hoop strength) of a balloon. Because a softer material generally has a relatively lower hoop strength, the presence of the lower durometer material forming the inner layer(s) of the balloon is not generally expected to provide a relatively higher modulus balloon. However, a multilayered balloon of the disclosed subject matter can have a higher modulus than, and a rupture pressure which is not substantially less than, a balloon formed of 100% of the highest durometer material.

The presence of the lower durometer material inner layer(s) does provide layers of increased softness, and therefore can provide a balloon that is softer and more flexible than a balloon formed of 100% of the highest durometer material.

A balloon of the disclosed subject matter can arrange layers so that the highest durometer material has on an inner surface thereof a layer of a lower durometer material, and configures the layers to provide for a maximized BUR which produces an improved combination of characteristics including a very low compliance. However, with the inner layer(s) of the balloon of the disclosed subject matter optimized for compliance purposes as discussed above, certain embodiments of a balloon of the disclosed subject matter has an outer-most layer of a relatively soft material, to, for example, enhance stent retention, it desired.

The compliance of the balloon should be understood to refer to the degree to which the polymeric wall of the balloon stretches/distends as the balloon expands beyond the nominal diameter of the balloon. The compliance curve expresses the balloon outer diameter as a function of increasing inflation pressure in millimeters/atmospheres (mm/atm), so that a steeper curve or section of the curve indicates a higher compliance than a flatter curve. The term "noncompliant", should be understood to mean a balloon with compliance of not greater than about 0.03 mm/atm, and in an embodiment not greater than about 0.025 mm/atm. In contrast, compliant balloons typically have a compliance of greater than about 0.045 mm/atm. A noncompliant balloon of the disclosed subject matter generally has a compliance above nominal of about 0.01 to about 0.02 mm/atm, for a 3.0 mm diameter balloon. The compliance of the balloon is typically about 25% to about 50% less than the compliance of a balloon with a similar wall thickness but made from 100% of the first (e.g., highest durometer) material.

In certain embodiments, the polymeric material of the first layer and the polymeric material of the second layer of the multilayered balloon are elastomers, which typically have a lower flexural modulus than nonelastomers. Elastomeric polymers suitable for forming the first and/or second layer of the multilayered balloon typically have a flexural modulus of about 40 kpsi to about 110 kpsi. Thus, unlike nonelastomeric materials such as PET, the multilayered noncompliant balloon of the disclosed subject matter can be formed of one or more elastomers which provide for improved balloon flexibility.

Balloon in accordance with the disclosed subject matter can be formed by any suitable method. For example, one method generally comprises selecting a first and a second polymeric material, the second polymeric material having been determined to have a higher maximum attainable BUR than the first polymeric material, and forming a multilayered tube having a first layer of the first polymeric material, and a second layer of the second polymeric material wherein the second layer is an inner layer relative to the first layer. The maximum attainable BUR of a polymeric material is typically determined experimentally, although characteristics such as the ultimate tensile strength and elongation to break of the material maybe indicative at least for some materials (e.g., a material having a relatively higher ultimate tensile strength and elongation to break is expected, in general, to have a higher maximum BUR). The inner diameter of each layer of the multilayered tube is selected so that the ratio of the inner diameter of the balloon mold and the inner diameter of the layer of the multilayered tube (prior to being radially expanded in the balloon mold) is substantially at a maximum blow-up-ratio for the polymeric material forming the layer. Thus, the method includes forming the blow-molded multilayered balloon by radially expanding the multilayered tube in a mold, so that radially expanding the tube to the mold inner diameter radially expands each layer substantially to the maximum blow-up-ratio of the polymeric material forming the layer, such that the multilayered balloon has a lower compliance above the nominal working diameter than a balloon consisting of the first elastomeric polymeric material.

The multilayered balloon of the disclosed subject matter provides a very low compliance for controlled balloon expansion, without compromising relatively high flexibility and softness for excellent ability to track the patient's vasculature and cross lesions. As a result, the adjustable balloon catheter of the disclosed subject matter has improved performance due to the flexibility, softness, and controlled expansion of the balloon. The balloon provides the surprising result of a very low compliance from the addition of the lower durometer (softer) second material. Consequently, a multilayered balloon of the disclosed subject matter will provide a much lower compliance than a balloon with the same wall thickness but made from just the higher durometer (stiffer) material, or will provide a much thinner walled balloon but without the expected increase in compliance.

In accordance with another aspect of the disclosed subject matter, a therapeutic agent can be disposed on the expandable member. In this manner, the outer tubular member can protect the therapeutic agent during delivery of the catheter to the selected site. Additionally, the amount and location of drug released will be a function of the exposed length of the expandable member. The therapeutic agent can be for the treatment of a disease. Examples of suitable therapeutic agents include anti-proliferative, anti-inflammatory, antineoplastic, antiplatelet, anti-coagulant, anti-fibrin, antithrombotic, antimitotic, antibiotic, antiallergic and antioxidant compounds. Such therapeutic agents can be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent including streptokinase and tissue plasminogen activator, an antigen, a hormone, a growth factor, a ribozyme, and a retroviral vector.

In certain embodiments, however, the therapeutic agents include a cytostatic drug. The term "cytostatic" as used herein means a drug that mitigates cell proliferation but allows cell migration. These cytostatic drugs, include for the purpose of illustration and without limitation, macrolide antibiotics, rapamycin, everolimus, zotaroliumus, biolimus, ternsirolimus, deforolimus, novolimus, myolimus, structural derivatives and functional analogues of rapamycin, structural derivatives and functional analogues of everolimus, structural derivatives and functional analogues of zotarolimus and any marcrolide immunosuppressive drugs. The term "cytotoxic" as used herein means a drug used to inhibit cell growth, such as chemotherapeutic drugs. Some non-limiting examples of cytotoxic drugs include vincristine, actinomycin, cisplatin, taxanes, paclitaxel, and protaxel. Other drugs include dexamethasone, statins, sirolimus, and tacrolimus.

In addition to the therapeutic agent, any of a variety of fluid compositions can be applied to the expandable member. The fluid can include compounds or additives, such as polymers, binding agents, plasticizers, solvents, surfactants, additives, chelators, fillers, excipients, and the like, or combinations thereof. Suitable excipients, binding agents and other components include those described in detail in U.S. patent application Ser. No. 12/636,079, which is hereby incorporated by reference in its entirety. In certain embodiments, excipients include poly(ethylene glycol) (PEG), polyvinylpyrrolidone (PVP), polyoxyethylene sorbitan monooleate (tweens), poloxamer triblock copolymers of poly(ethylene oxide)-poly(propylene oxide)-poly(ethylene oxide) (Pluronics), carboxymethyl cellulose (CMC), and PEG phospholipids such as 1,2-distearolyl-sn-glycero-3-phosphoethanolamine-N-(methoxy(polyethylene glycol)-2000) (PEG-PE). In certain embodiments, plasticizers include PEG, propylene glycol, N-methylpyrrolidone (NMP), glycerin, and tweens. Examples of possible compounds include zotarolimus, PVP and glycerol. In certain embodiments the therapeutic agent can be provided in liquid form or dissolved in a suitable solvent. In another embodiment, the therapeutic agent is provided as a particulate and mixed in a suitable carrier for application as a fluid.

The fluid compositions, such as the therapeutic agents, can be applied to the expandable member using a variety of know techniques, such as spraying (air-atomization, ultrasonic, electrostatic, piezoelectric, etc.), spray drying, pneumatic spray, spray with patterning, electro spinning, direct fluid application, dip-coating, spin-coating, pipette coating, syringe coating, vapor deposition, roll coating, micro-droplet coating, ultrasonic atomization, or other means as known to those skilled in the art. The coating can be applied over at least a length or the entirety of the expandable member. By way of example, and not limitation, certain coating processes that can be used with the instant disclosed subject matter are described in U.S. Pat. No. 6,669,980 to Hansen; U.S. Pat. No. 7,241,344 to Worsham; U.S. Publication No. 2004/0234748 to Stenzel; and U.S. Patent Application Ser. No. 61/345,575, the entire disclosures of which are hereby incorporated by reference. In accordance with an embodiment of the disclosed subject matter, the coating can be applied to either a folded or inflated balloon. Furthermore, the coating can be directly applied into the folds of the folded balloons. The coating characteristics are affected by process variables. For example, for dip-coating process, coating quality and thickness can vary as an effect of variables such as number, rate, and depth of dips along with drying time and temperature.

In accordance with another aspect of the disclosed subject matter, the expandable member can include microcapsules on its outer surface. In this regard, the microcapsules are configured to encompass the coating and/or therapeutic agent. Upon inflation of the expandable member the microcapsules located on the surface of the expandable member contact the tissue of the arterial wall. Alternatively, the microcapsules can be formed in the wall of the expandable member surface or on the tissue engaging member. The coating and/or therapeutic agent can be released from the microcapsules by fracturing of the microcapsules and/or diffusion from the microcapsule into the arterial wall. The microcapsules can be fabricated in accordance with the methods disclosed in U.S. Pat. No. 5,102,402 to Dror or U.S. Pat. No. 6,129,705 to Grantz and the patents referenced therein, each of which is incorporated herein by reference in its entirety.

The markers can include any suitable material. For example, the markers can be constructed of a polymer filled or impregnated with a radiopaque material and can further include, but not limited to, PPS, Tungsten, and glass fiber combination; PA12 and ceramics combination; PEEK and ceramics combination; and a PBT and ceramics combination.

While the disclosed subject matter is described herein in terms of certain preferred embodiments, those skilled in the art will recognize that various modifications and improvements can be made to the disclosed subject matter without departing from the scope thereof. Additional features known in the art likewise can be incorporated, such as disclosed in U.S. Pat. No. 7,799,065 to Pappas, which is incorporated in its entirety by reference herein. Moreover, although individual features of an embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the various embodiments depicted and claimed, the disclosed subject matter is also directed to other embodiments having any other possible combination of the features disclosed and claimed herein. As such, the particular features presented herein can be combined with each other in other manners within the scope of the disclosed subject matter such that the disclosed subject matter includes any suitable combination of the features disclosed herein. Furthermore, although reference is made to a medical device, stent, or expandable member throughout this disclosure, other suitable devices and implants likewise can be delivered using the catheter and system disclosed herein. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

For example, and further to the detailed description above, the disclosed subject matter herein can include one or more of the following:

Embodiment 1

A catheter comprising: an inner tubular member having a proximal end portion, a distal end portion and an exterior surface, the inner tubular member further having a fluid lumen and an inflation lumen defined therein, the fluid lumen having a fluid flow port defined by the exterior surface along the distal end portion of the inner tubular member; an outer tubular member movable relative to the inner tubular member, the outer tubular member having a proximal end, a distal end and an interior surface directed toward the exterior surface of the inner tubular member; an expandable member coupled to the distal end portion of the inner tubular member and having an inner chamber in fluid communication with the inflation lumen, the expandable member transitionable between a deflated configuration and an inflated configuration; a proximal seal extending from the interior surface of the outer tubular member toward the exterior surface of the inner tubular member, the proximal seal located proximal to the fluid flow port; a distal seal extending from the exterior surface of the inner tubular member toward the interior surface of the outer tubular member, the distal seal located distal to the fluid flow port; and a pressure chamber defined by the proximal seal, the distal seal, the exterior surface of the inner tubular member and interior surface of the outer tubular member, with the pressure chamber in fluid communication with the fluid flow port, wherein fluid introduced through the fluid flow port and into the pressure chamber applies a force on the proximal seal to urge the outer tubular member in a proximal direction.

Embodiment 2

The catheter of Embodiment 1, wherein the inner tubular member further includes a guidewire lumen defined therein.

Embodiment 3

The catheter of any of the foregoing Embodiments, wherein the guidewire lumen is defined by guidewire tube disposed within the fluid lumen.

Embodiment 4

The catheter of any of the foregoing Embodiments, wherein the inner tubular member further comprises a strengthening member disposed along a length corresponding to the pressure chamber.

Embodiment 5

The catheter of any of the foregoing Embodiments, further comprising a marker secured to the inner tubular member to seal a distal end of the fluid lumen distal of the fluid flow port.

Embodiment 6

The catheter of any of the foregoing Embodiments, wherein the fluid lumen is configured to receive a guidewire, the fluid lumen further comprising proximal and distal guidewire seals to seal around a guidewire disposed therethrough.

Embodiment 7

The catheter of any of the foregoing Embodiments, wherein the distal end of the outer tubular member further comprises a marker.

Embodiment 8

The catheter of any of the foregoing Embodiments, further comprising a proximal stopper disposed proximal to the pressure chamber, wherein the outer tubular member is movable in a proximal direction up to engagement of the proximal stopper.

Embodiment 9

The catheter of any of the foregoing Embodiments, wherein the proximal stopper inhibits movement of the outer tubular member in the proximal direction.

Embodiment 10

The catheter of any of the foregoing Embodiments, further comprising a proximal adapter, wherein the proximal stopper is disposed distal to the proximal adapter.

Embodiment 11

The catheter of any of the foregoing Embodiments, wherein the expandable member further defines a working length thereof and includes a proximal portion proximal to the working length, the proximal portion remaining with the outer tubular member when positioned in a retracted position.

Embodiment 12

The catheter of any of the foregoing Embodiments, wherein the expandable member has a folded arrangement in the deflated configuration, the proximal portion remaining at least partially folded within the outer tubular member in the inflated configuration.

Embodiment 13

The catheter of any of the foregoing Embodiments, wherein the medical device is crimped about the expandable member in the folded arrangement.

Embodiment 14

The catheter of any of the foregoing Embodiments, wherein the expandable member includes a semicompliant material.

Embodiment 15

The catheter of Embodiments 1 through 13, wherein the expandable member includes compliant material.

Embodiment 16

The catheter of any of the foregoing Embodiments, wherein the expandable member includes a multilayer construction.

Embodiment 17

The catheter of any of the foregoing Embodiments, further comprising a stent disposed on the expandable member having an initial delivery condition and a deployed condition, wherein the medical device is transitionable to the deployed condition when fluid introduced through the inflation lumen and into the inner chamber of the expandable member inflates the expandable member to the inflated configuration.

Embodiment 18

The catheter of any of the foregoing Embodiments, wherein the expandable member further includes a therapeutic agent disposed thereon.

Embodiment 19

The catheter of any of the foregoing Embodiments, further comprising a second inflation lumen and a second expandable member coupled to the distal end portion of the inner tubular member and having a second inner chamber in fluid communication with the second inflation lumen, the second expandable member transitionable between a deflated configuration and an inflated configuration.

Embodiment 20

The catheter of any of the foregoing Embodiments, further comprising a second medical device disposed on the second expandable member having an initial delivery condition and a deployed condition, wherein the second medical device is transitionable to the deployed condition when fluid introduced through the second inflation lumen and into the second inner chamber of the second expandable member inflates the second expandable member to the inflated configuration.

Embodiment 21

The catheter of the Embodiments 1 through 16 and 18 through 20, further comprising a stent disposed on the expandable member having an initial delivery condition and a deployed condition, wherein the medical device is transitionable to the deployed condition when fluid introduced through the inflation lumen and into the inner chamber of the expandable member inflates the expandable member to the inflated configuration, wherein at least one of the medical device and the second expandable member further includes a therapeutic agent disposed thereon.

Embodiment 22

A catheter comprising: an inner tubular member having a proximal end portion, a distal end portion and an exterior surface, the inner tubular member further having a fluid lumen defined therein, the fluid lumen having a fluid flow port defined by the exterior surface along the distal end portion of the inner tubular member, the fluid lumen further including a directional control valve fluidly coupled with the fluid flow port, the directional control valve having a first position and a second position; an outer tubular member movable relative to the inner tubular member, the outer tubular member having a proximal end, a distal end and an interior surface directed toward the exterior surface of the inner tubular member; an expandable member coupled to the distal end portion of the inner tubular member and having an inner chamber in fluid communication with the fluid lumen, the expandable member transitionable between a deflated configuration and an inflated configuration; a proximal seal extending from the interior surface of the outer tubular member toward the exterior surface of the inner tubular member, the proximal seal located proximal to the fluid flow port; a distal seal extending from the exterior surface of the inner tubular member toward the interior surface of the outer tubular member, the distal seal located distal to the fluid flow port; and a pressure chamber defined by the proximal seal, the distal seal, the exterior surface of the inner tubular member and interior surface of the outer tubular member, with the pressure chamber in fluid communication with the fluid flow port, wherein the directional control valve in the first position directs fluid introduced in the fluid lumen through the fluid flow port into the pressure chamber to apply a force on the proximal seal to urge the outer tubular member in a proximal direction and wherein the directional control valve in the second position directs fluid through the fluid lumen into the inner chamber of the expandable member to inflate the expandable member to the inflated configuration.

Embodiment 23

The catheter of the Embodiment 22, wherein the catheter further comprises a medical device disposed on the expandable member having an initial delivery condition and a deployed condition, wherein the medical device is transitionable to the deployed condition when fluid introduced through into the inner chamber of the expandable member inflates the expandable member to the inflated configuration.

What is claimed is:

1. A catheter comprising:
an inner tubular member having a proximal end portion, a distal end portion and an exterior surface, the inner tubular member further having a fluid lumen defined therein, the fluid lumen having a fluid flow port defined by the exterior surface along the distal end portion of the inner tubular member, the fluid lumen further including a directional control valve fluidly coupled with the fluid flow port, the directional control valve having a first position and a second position;
an outer tubular member movable relative to the inner tubular member, the outer tubular member having a proximal end, a distal end and an interior surface directed toward the exterior surface of the inner tubular member;
an expandable member coupled to the distal end portion of the inner tubular member and having an inner chamber in fluid communication with the fluid lumen, the expandable member transitionable between a deflated configuration and an inflated configuration;
a proximal seal extending from the interior surface of the outer tubular member toward the exterior surface of the inner tubular member, the proximal seal located proximal to the fluid flow port;
a distal seal extending from the exterior surface of the inner tubular member toward the interior surface of the outer tubular member, the distal seal located distal to the fluid flow port; and
a pressure chamber defined by the proximal seal, the distal seal, the exterior surface of the inner tubular member and interior surface of the outer tubular member, with the pressure chamber in fluid communication with the fluid flow port, wherein the directional control valve in the first position directs fluid through the fluid flow port into the pressure chamber to apply a force on the proximal seal to urge the outer tubular member in a proximal direction and wherein the directional control valve in the second position subsequent to the outer tubular member being urged in the proximal direction directs fluid through the fluid lumen into the inner chamber of the expandable member to inflate the expandable member to the inflated configuration.

2. The catheter according to claim 1, wherein the inner tubular member further includes a guidewire lumen defined therein.

3. The catheter according to claim 2, wherein the guidewire lumen is defined by a guidewire tube disposed within the fluid lumen.

4. The catheter according to claim 1, wherein the inner tubular member further comprises a strengthening member disposed along a length corresponding to the pressure chamber.

5. The catheter according to claim 1, further comprising a marker secured to the inner tubular member to seal a distal end of the fluid lumen distal of the fluid flow port.

6. The catheter according to claim 1, wherein the fluid lumen is configured to receive a guidewire, the fluid lumen further comprising proximal and distal guidewire seals to seal around a guidewire disposed therethrough.

7. The catheter according to claim 1, wherein the distal end of the outer tubular member further comprises a marker.

8. The catheter according to claim 1, further comprising a proximal stopper disposed proximal to the pressure chamber, wherein the outer tubular member is movable in a proximal direction up to engagement of the proximal stopper.

9. The catheter according to claim 8, wherein the proximal stopper inhibits movement of the outer tubular member in the proximal direction.

10. The catheter according to claim 8, further comprising a proximal adapter, wherein the proximal stopper is disposed distal to the proximal adapter.

11. The catheter according to claim 1, wherein the expandable member further defines a working length thereof and includes a proximal portion proximal to the working length, the proximal portion remaining with the outer tubular member when positioned in a retracted position.

12. The catheter according to claim 11, wherein the expandable member has a folded arrangement in the deflated configuration, the proximal portion remaining at least partially folded within the outer tubular member with an unfolded portion outside the outer tubular member in the inflated configuration, and wherein the proximal portion remaining at least partially folded is configured to facilitate refolding of the unfolded portion when the expandable member is deflated and the outer tubular member is moved distally.

13. The catheter according to claim 12, wherein a medical device is crimped about the expandable member in the folded arrangement.

14. The catheter according to claim 1, wherein the expandable member includes a semicompliant material.

15. The catheter according to claim 1, wherein the expandable member includes compliant material.

16. The catheter according to claim 1, wherein the expandable member includes a multilayer construction.

17. The catheter according to claim 1, further comprising a stent disposed on the expandable member having an initial delivery condition and a deployed condition, wherein the stent is transitionable to the deployed condition when the directional control valve in the second position directs fluid into the inner chamber of the expandable member to inflate the expandable member to the inflated configuration.

18. The catheter according to claim 1, wherein the expandable member further includes a therapeutic agent disposed thereon.

19. The catheter according to claim 1, further comprising a second expandable member coupled to the distal end portion of the inner tubular member and having a second inner chamber, the second expandable member transitionable between a deflated configuration and an inflated configuration.

20. The catheter according to claim 19, further comprising a medical device disposed on the second expandable member having an initial delivery condition and a deployed condition, wherein the medical device is transitionable to the deployed condition when fluid introduced into the second inner chamber of the second expandable member inflates the second expandable member to the inflated configuration.

21. The catheter according to claim 19, further comprising a stent disposed on the expandable member having an initial delivery condition and a deployed condition, wherein the stent is transitionable to the deployed condition when fluid introduced into the inner chamber of the expandable member inflates the expandable member to the inflated configuration, wherein at least one of the medical device and the stent further includes a therapeutic agent disposed thereon.

22. The catheter according to claim 1, wherein the directional control valve is disposed proximate the fluid flow port.

* * * * *